(12) United States Patent
Lindell et al.

(10) Patent No.: US 7,819,793 B2
(45) Date of Patent: Oct. 26, 2010

(54) APPARATUS FOR SEPARATING A COMPOSITE LIQUID INTO AT LEAST TWO COMPONENTS

(75) Inventors: Hans Lindell, Save (SE); Thomas L. Menhennett, Louisville, CO (US); Johan-Petter Hogström, Hägersten (SE); Per-Olov Jan Lundberg, Karlskoga (SE); Brian M. Holmes, Lakewood, CO (US); Charles L. Hake, Arvada, CO (US); Daniel A. Joseph, Golden, CO (US)

(73) Assignee: CaridianBCT, Inc., Lakewood, CO (US)

( * ) Notice: Subject to any disclaimer, the term of this patent is extended or adjusted under 35 U.S.C. 154(b) by 826 days.

(21) Appl. No.: 11/751,748

(22) Filed: May 22, 2007

(65) Prior Publication Data

US 2007/0284320 A1 Dec. 13, 2007

Related U.S. Application Data

(60) Provisional application No. 60/804,116, filed on Jun. 7, 2006.

(51) Int. Cl.
*B04B 9/14* (2006.01)
*B04B 13/00* (2006.01)

(52) U.S. Cl. .............................. 494/82; 494/21; 494/45

(58) Field of Classification Search ................... 494/21, 494/45, 82
See application file for complete search history.

(56) References Cited

U.S. PATENT DOCUMENTS

| 414,642 | A | 2/1889 | Herrick |
|---|---|---|---|
| 3,297,244 | A | 1/1967 | Hein |
| 3,326,458 | A | 6/1967 | Merman et al. |
| 3,679,128 | A | 7/1972 | Unger et al. |
| 3,708,110 | A | 1/1973 | Unger et al. |
| 3,724,747 | A | 4/1973 | Unger et al. |
| 3,737,096 | A | 6/1973 | Jones et al. |
| 3,858,796 | A | 1/1975 | Unger et al. |
| 3,987,961 | A | 10/1976 | Sinn et al. |
| 4,146,172 | A | 3/1979 | Cullis et al. |
| 4,389,207 | A | 6/1983 | Bacehowski et al. |
| 4,405,079 | A | 9/1983 | Schoendorfer |
| 4,421,503 | A | 12/1983 | Latham, Jr. et al. |
| 4,482,342 | A | 11/1984 | Lueptow et al. |
| 4,720,284 | A | 1/1988 | McCarty |
| 4,850,995 | A | 7/1989 | Tie et al. |

(Continued)

FOREIGN PATENT DOCUMENTS

DE 2545283 A1 4/1977

(Continued)

OTHER PUBLICATIONS

International Search Report for PCT/US2007/069417, mailed May 2, 2008.

*Primary Examiner*—Walter D Griffin
*Assistant Examiner*—Christopher K VanDeusen
(74) *Attorney, Agent, or Firm*—Edna M. O'Connor; John R. Herkling; Laura B. Arciniegas

(57) ABSTRACT

An apparatus for separating blood into blood components using a separation vessel satellite bags mounted on a centrifuge rotor and a balancing assembly for the centrifuge to compensate for changes to the center of gravity.

30 Claims, 16 Drawing Sheets

U.S. PATENT DOCUMENTS

| | | |
|---|---|---|
| 4,990,132 A | 2/1991 | Unger et al. |
| 5,114,396 A | 5/1992 | Unger et al. |
| 5,427,695 A | 6/1995 | Brown |
| 5,543,062 A | 8/1996 | Nishimura |
| 5,632,906 A | 5/1997 | Ishida et al. |
| 5,637,082 A | 6/1997 | Pages et al. |
| 5,723,050 A | 3/1998 | Unger et al. |
| 5,738,644 A | 4/1998 | Holmes et al. |
| 5,874,208 A | 2/1999 | Unger |
| 5,904,355 A | 5/1999 | Powers et al. |
| 5,964,724 A | 10/1999 | Rivera et al. |
| 6,039,711 A | 3/2000 | Headley et al. |
| 6,082,151 A | 7/2000 | Wierzba et al. |
| 6,132,354 A | 10/2000 | Ohtsu et al. |
| 6,261,217 B1 | 7/2001 | Unger et al. |
| 6,296,602 B1 | 10/2001 | Headley |
| 6,315,706 B1 | 11/2001 | Unger et al. |
| 6,333,912 B1 | 12/2001 | Sohn |
| 6,348,031 B1 | 2/2002 | Unger et al. |
| 6,439,577 B2 | 8/2002 | Jorgensen et al. |
| 6,558,307 B2 | 5/2003 | Headley |
| 6,605,223 B2 | 8/2003 | Jorgensen et al. |
| 6,641,552 B1 | 11/2003 | Kingsley et al. |
| 6,656,105 B2 | 12/2003 | Hogberg et al. |
| 7,166,217 B2 | 1/2007 | Holmes et al. |
| 2001/0051569 A1 | 12/2001 | Headley |
| 2002/0020680 A1 | 2/2002 | Jorgensen |
| 2002/0082153 A1* | 6/2002 | Jorgensen et al. ............... 494/2 |
| 2002/0119880 A1 | 8/2002 | Hogberg et al. |
| 2004/0026341 A1 | 2/2004 | Hogberg et al. |
| 2004/0052201 A1 | 3/2004 | Hong et al. |
| 2004/0058794 A1 | 3/2004 | Dolecek et al. |
| 2004/0104182 A1* | 6/2004 | Holmes et al. ............... 210/787 |
| 2005/0045567 A1 | 3/2005 | Holmes et al. |

FOREIGN PATENT DOCUMENTS

| | | |
|---|---|---|
| DE | 10355026 | 7/2005 |
| EP | 0 499891 B1 | 8/1992 |
| EP | 0587257 | 3/1994 |
| EP | 0 771 569 B1 | 5/1997 |
| JP | 02 203949 | 8/1990 |
| WO | WO92/00145 A1 | 1/1992 |
| WO | WO98/35757 | 8/1998 |
| WO | WO2005/030398 | 4/2000 |
| WO | WO01/97943 A1 | 12/2001 |
| WO | WO2004/018021 | 3/2004 |

* cited by examiner

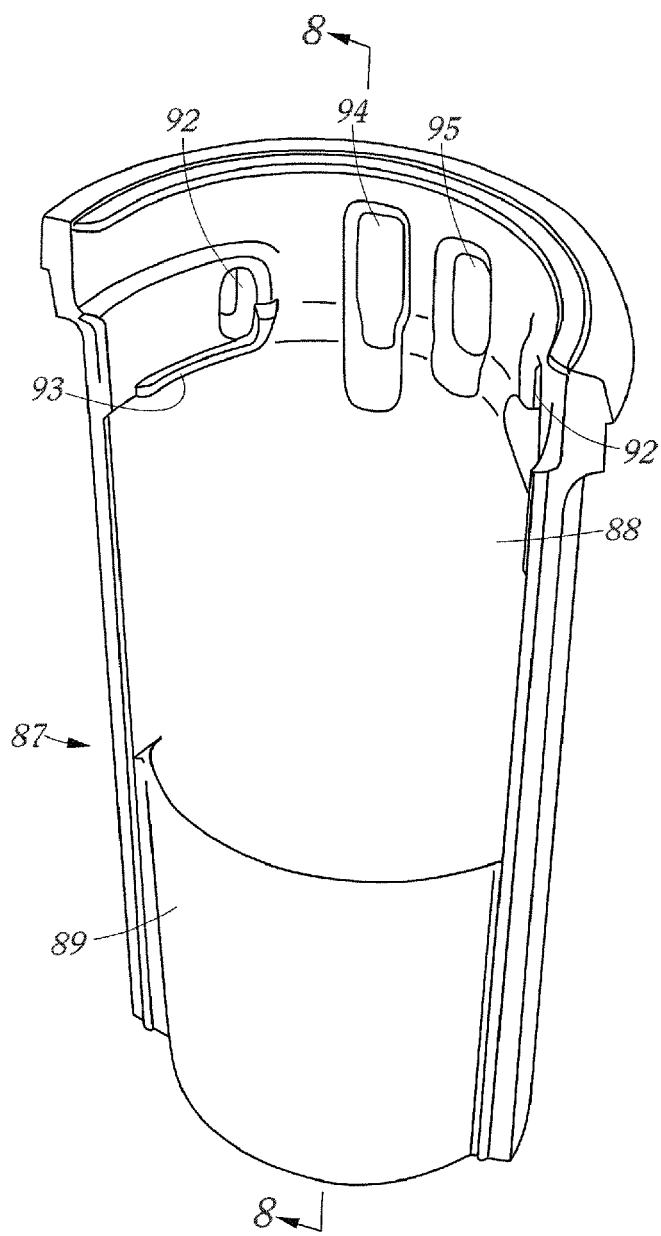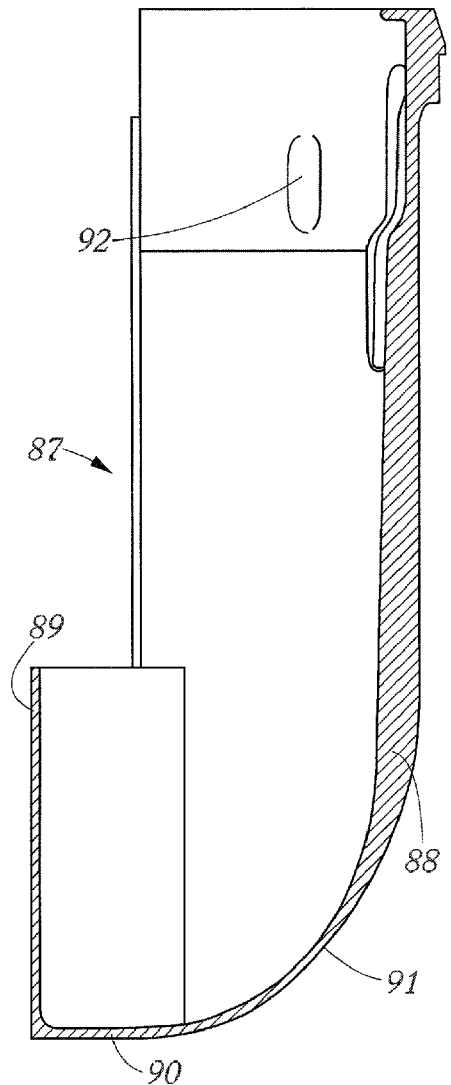
FIG. 7
FIG. 8

APPARATUS FOR SEPARATING A COMPOSITE LIQUID INTO AT LEAST TWO COMPONENTS

CROSS REFERENCE TO RELATED APPLICATIONS

This application claims the benefit of United States Provisional Application No. 60/804,116, filed Jun. 7, 2006.

BACKGROUND OF THE INVENTION

Field of the Invention

The present invention concerns an apparatus and a method for separating at least one volume of composite liquid into at least two components.

The apparatus and method of the invention are particularly appropriate for the separation of biological fluids comprising an aqueous component and one or more cellular components. For example, potential uses of the invention include: extracting a plasma component, a first cellular component including platelets and mononuclear cells, and a second cellular component including red blood cells and granulocytes from a volume of whole blood or washing thawed glycerolized red blood cells in order to extract therefrom red blood cells ready for use.

BRIEF SUMMARY OF THE INVENTION

International patent application WO 2004/018021 describes a method and an apparatus for separating a volume of whole blood into either a plasma component and a red blood cell component or a plasma component, a red blood cell component and a platelet component.

The apparatus comprises a centrifuge adapted to cooperate with an annular separation bag for whole blood, which is connected to either a plasma component bag and a red blood cell component bag or a plasma component bag, a red blood cell component bag and a platelet component bag. The centrifuge includes: a rotor for spinning the separation bag and centrifuging the whole blood contained therein, the rotor having a turntable for supporting the separation bag and a central compartment for containing the component bags connected to the separation bag; and a squeezing system for squeezing the separation bag and causing the transfer of the plasma component from the separation bag into the plasma component bag, of the red blood cell component into the red blood cell component bag and, as the case may be, of the platelet component into the platelet component bag.

An object of the invention is to design a centrifugation apparatus that can perform an optimized separation process for separating, in a minimum amount of time, a composite fluid, such as whole blood, into at least two high quality components.

According to the invention, an apparatus for separating at least one volume of a composite liquid into at least a first component and a second component comprises: a centrifuging means having a rotation axis, comprising: a first containing means for storing a liquid at a distance from the rotation axis, whereby the storage of a liquid in the first containing means can cause an unbalance of the centrifuging means; a second containing means for storing a liquid at a distance from the rotation axis, whereby the storage of a liquid in the second containing means can cause an unbalance of the centrifuging means; a liquid transferring means for transferring a liquid between containing means whereby the transfer of a liquid can cause an unbalance of the centrifuging means; and a balancing means for substantially neutralizing an unbalance of the centrifuging means as it occurs.

According to the invention, a balancing assembly for a centrifuging means comprising: a plurality of ponderous satellites; a housing for containing the ponderous satellites and defining a circular orbit along which the ponderous satellites can move substantially freely; and a plurality of stopping or parking means temporarily stopping or parking the ponderous satellites when the centrifuging means does not rotate and the balancing assembly is inclined to no more than a predetermined angle with respect to a horizontal plane, and for allowing a movement of the ponderous satellites in the housing when the centrifuging means is rotating at a speed that is above a determined speed.

According to the invention, a method is also provided for separating a volume of composite liquid into at least a first component and a second component using a rotor having a rotation axis and comprising a turntable for supporting a separation bag and a central container for receiving at least one satellite bag connected to the separation bag; the method comprises the steps of: providing a separation bag fluidly connected to at least one satellite bag containing a volume of composite liquid; securing the separation bag to the turntable; securing the at least one satellite bag within the central container so that a lower portion thereof is closer to the rotation axis than an upper portion thereof, which is connected to the separation bag, and so that a content of the at least one satellite bag drains under centrifugation forces into the separation bag when the rotor is rotated at a transfer speed; rotating the rotor at the transfer speed so as to transfer at least a fraction of the volume of liquid from the at least one satellite bag into the separation bag; and substantially neutralizing an unbalance of the rotor caused by the liquid in the central container at a distance from the rotation axis.

Other features and advantages of the invention will appear from the following description and accompanying drawings, which are to be considered illustrative only.

BRIEF DESCRIPTION OF THE DRAWINGS

In the accompanying drawings:

FIG. 7 is a perspective view of the bag cradle of FIG. 6;

FIG. 8 is a cross section view of the bag cradle of FIG. 7, along a diametral plane;

DETAILED DESCRIPTION OF THE INVENTION

For the sake of clarity, the invention will be described with respect to two specific uses, namely the separation of whole blood into two or three components, and the washing of thawed glycerolized red blood cells. It should be understood however that these specific uses are exemplary only.

Figure 1:
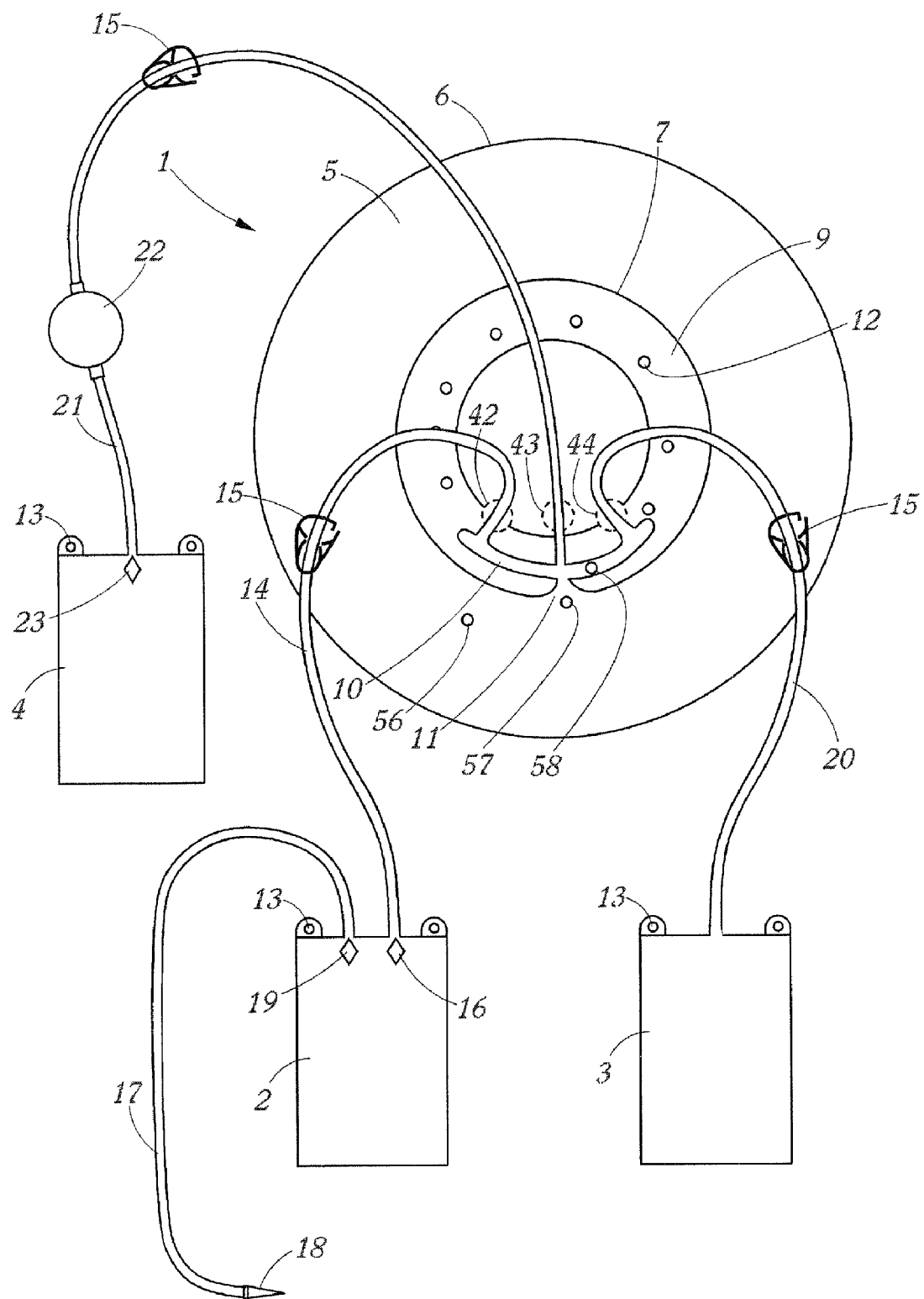
FIG. 1 is a schematic view of first set of separation and collection bags for cooperating with a separation apparatus.

FIG. 1 shows an example of a set of bags adapted to the separation of whole blood into a plasma component essentially comprising plasma, a first blood cell component essentially comprising mononuclear cells and platelets, and a second blood cell component essentially comprising red blood cells. This bag set comprises a flexible separation bag 1 and three flexible satellite bags 2, 3, 4 connected thereto. The separation bag 1 comprises an annular separation chamber 5 having a substantially circular outer edge 6 and an inner circular edge 7. The outer circular edge 6 and the inner circular edge 7 of the separation chamber 5 are substantially concentric. The separation bag 1 further comprises a semi-flexible disk-shaped connecting element 9 that is connected to the inner edge 7 of the annular chamber 5. The disk-shaped connecting element 9 comprises a distribution channel 10 embedded therein, which communicates through a passage 11 with the annular chamber 5. The distribution channel 10 substantially extends along an arc of a circle. The disk-shaped connecting element 9 comprises a series of holes 12 for securing the separation bag 1 to the rotor of a centrifuge.

The first satellite bag 2 has two purposes and is successively used as a blood collection bag 2 and as a mononuclear cell/platelet component bag. The first satellite bag is intended for initially receiving a volume of whole blood from a donor (usually about 450 ml) before the separation process, and the mononuclear cell/platelet component during the separation process. The first satellite bag 2 is flat, substantially rectangular, and comprises two reinforced ears at its upper corners having holes 13 for hanging the bag. It is connected to the separation bag 1 by a first transfer tube 14, fitted with a clamp 15. The first transfer tube 14 has a first end connected to the upper edge of the first satellite bag 2 and a second end connected to a first end of the distribution channel 10. The first satellite bag 2 contains a volume of anti-coagulant solution (typically about 63 ml of a solution of citrate phosphate dextrose for a blood donation of about 450 ml). A plug 16 removable from within the first satellite bag 2 (so-called "frangible pin", for example) blocks a liquid flow through the first transfer tube 14 and prevents the anti-coagulant solution from flowing from the first satellite bag 2 into the separation bag 1.

A collection tube 17 is connected at one end to the upper edge of the first satellite bag 2 and comprises, at the other end, a needle protected by a sheath 18. A frangible pin 19 removable from within the first satellite bag 2 plugs the downstream end of the collection tube 17 and prevents the anti-coagulant solution from flowing out of the first satellite bag 2 through the collection tube 17.

The second satellite bag 3 is intended for receiving a plasma component. It is flat, substantially rectangular, and comprises two reinforced ears at its upper corners having holes 13 for hanging the bag. It is connected by a second transfer tube 20 to the separation bag 1. The second transfer tube 20, which is fitted with a clamp 15, has a first end connected to the upper edge of the second satellite bag 3 and a second end connected to a second end of the distribution channel 10.

The third satellite bag 4 is intended for receiving a red blood cell component. It is flat, substantially rectangular, and comprises two reinforced ears at its upper corners having holes 13 for hanging the bag. It is connected by a third transfer tube 21 to the separation bag 1. The third transfer tube 21 has a first end connected to the upper edge of the third satellite bag 4 and a second end that is connected to the distribution channel 10 so as to face the passage 11 between the distribution channel 10 and the separation chamber 5. It comprises two segments respectively connected to the inlet and the outlet of a leuko-reduction filter 22. The tube segment connected to the separation bag 1 is fitted with a clamp 15. The filter 22 may be, for example, a filter of the type RC2D manufactured by Pall Corporation. Such a filter comprises a disk-shaped casing to which radial inlet and outlet ports are connected, in diametral opposition. The third satellite bag 4 contains a volume of storage solution for red blood cells. A plug 23 removable from within the third satellite bag 4 (so-called "frangible pin", for example) blocks a liquid flow through the third transfer tube 21 and prevents the storage solution from flowing from the third satellite bag 4 into the separation bag 1.

Variants of the separation bag 1 may include: a separation chamber 5 having an outer circular edge 6 and/or an inner circular edge 7 that are eccentric; a separation chamber 5 that comprises a radial wall extending from the inner edge 7 to the outer edge 6 so that the chamber 5, instead of being annular, is C-shaped; a separation chamber 5 having any shape including an inner edge and an outer edge (the inner edge being closer to the axis of the rotor of a centrifuge than the outer edge, when the separation bag is mounted on the rotor of a centrifuge), for example of the shape of a portion of annulus delimited by two lateral radial edge or a rectangular shape. In this variant, all the satellite bags may be connected to the inner edge of the separation bag.

Also the separation bag 1 can be shaped so as to fit either on a flat support surface or on a frusto-conical support surface of the rotor of a centrifuge.

Figure 2:
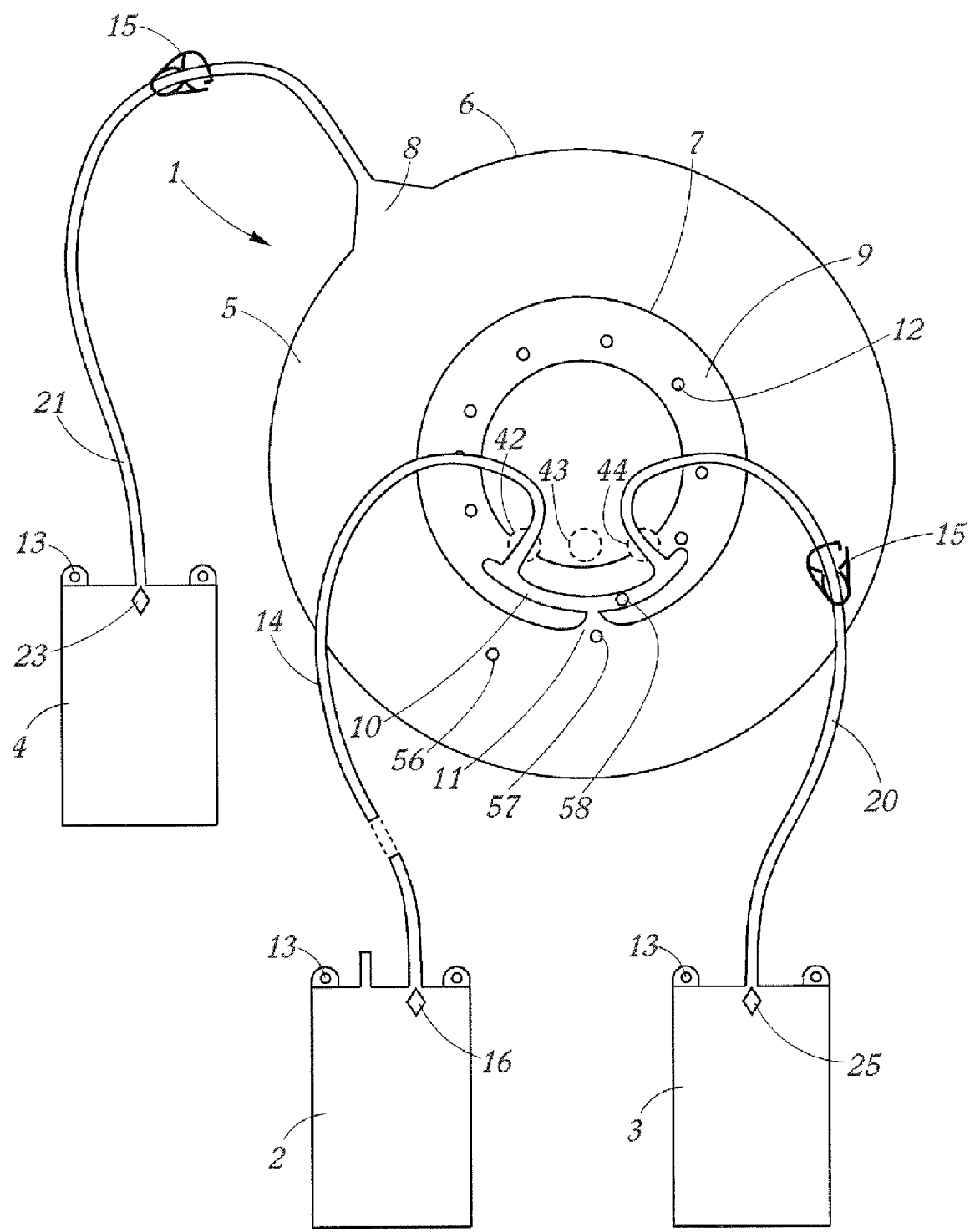
FIG. 2 is a schematic view of second set of separation and collection bags for cooperating with a separation apparatus.

FIG. 2 shows an example of a set of bags adapted to the washing of thawed glycerolized red blood cells. This bag set comprises a separation bag 1 and three satellite bags 2, 3, 4.

The separation bag 1 is identical to the separation bag shown in FIG. 1, save for the fact that the separation chamber 5 comprises a funnel like extension 8 protruding outwardly from its outer edge 6 for helping evacuate a content of the separation chamber 5 into the third satellite bag 4.

The first satellite bag 2 contains a volume of thawed glycerolized red blood cells (for example, 300 ml). It is identical to the second satellite bag 2 shown in FIG. 1, except that it is not pre-connected to the separation bag 1. It is connected through a sterile connection process to the first transfer tube 14 just before processing in the centrifuge.

The second satellite bag 3 contains a volume blood washing solution (for example, 700 ml for a volume of glycerolized red blood cells of 300 ml). A plug 25 removable from within (so-called "frangible pin", for example) blocks a liquid flow through the third transfer tube 20 and prevents the blood washing solution from flowing from the second satellite bag 3 into the separation bag 1.

The third satellite bag 4 is intended for receiving washed red blood cells. It is identical to the third satellite bag 4 shown in FIG. 1. The third transfer tube 21 connecting the third satellite bag 4 to the separation bag 1 is not fitted with a leuko-reduction filter.

The bags and the tubes of the first and second bag sets shown in FIGS. 1 and 2 are all made of flexible plastic material appropriate to getting in contact with blood and blood components.

Figure 3:
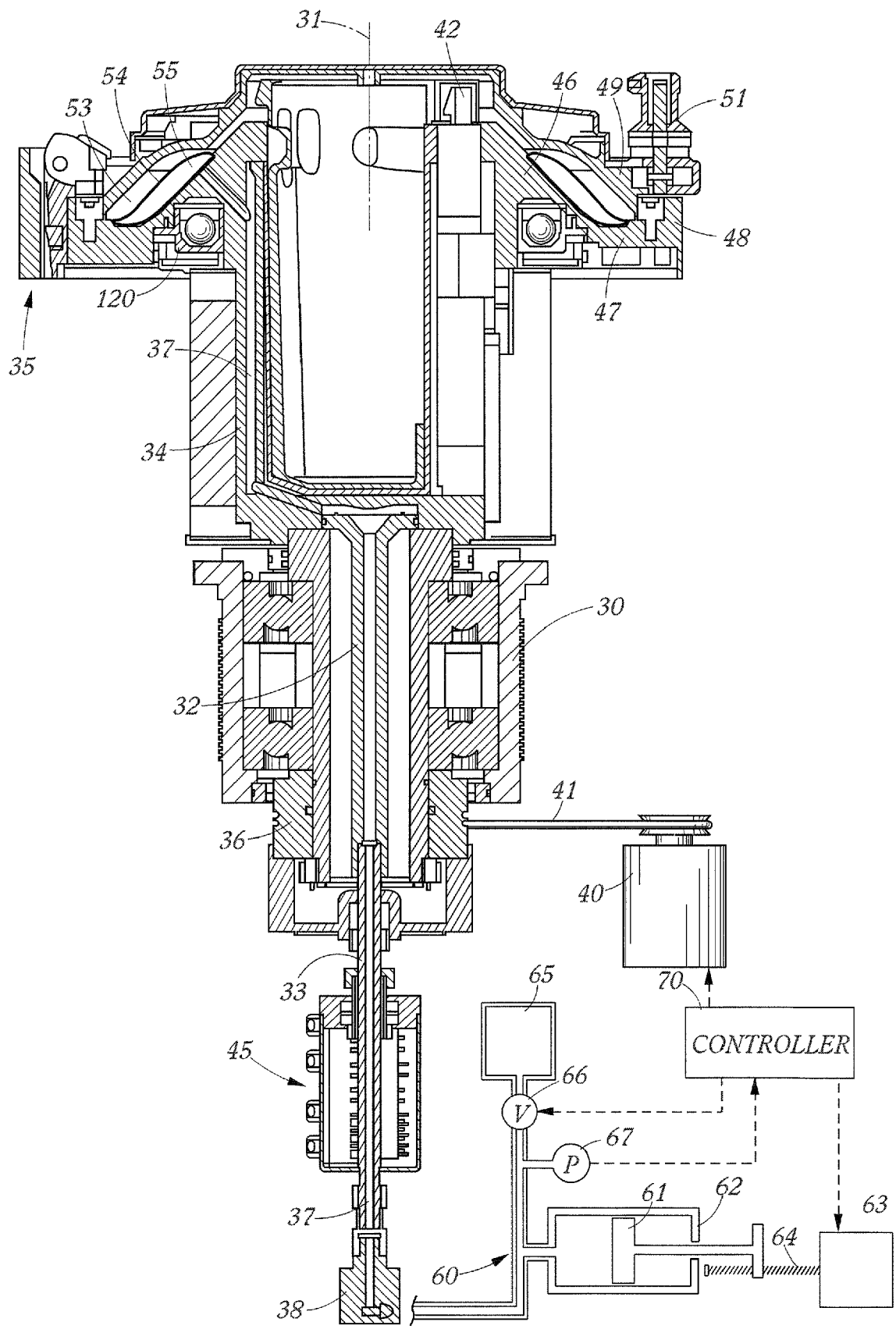
FIG. 3 is a schematic view, partly in cross-section along a diametral plane, of a first embodiment of a separation apparatus.
Figure 4:
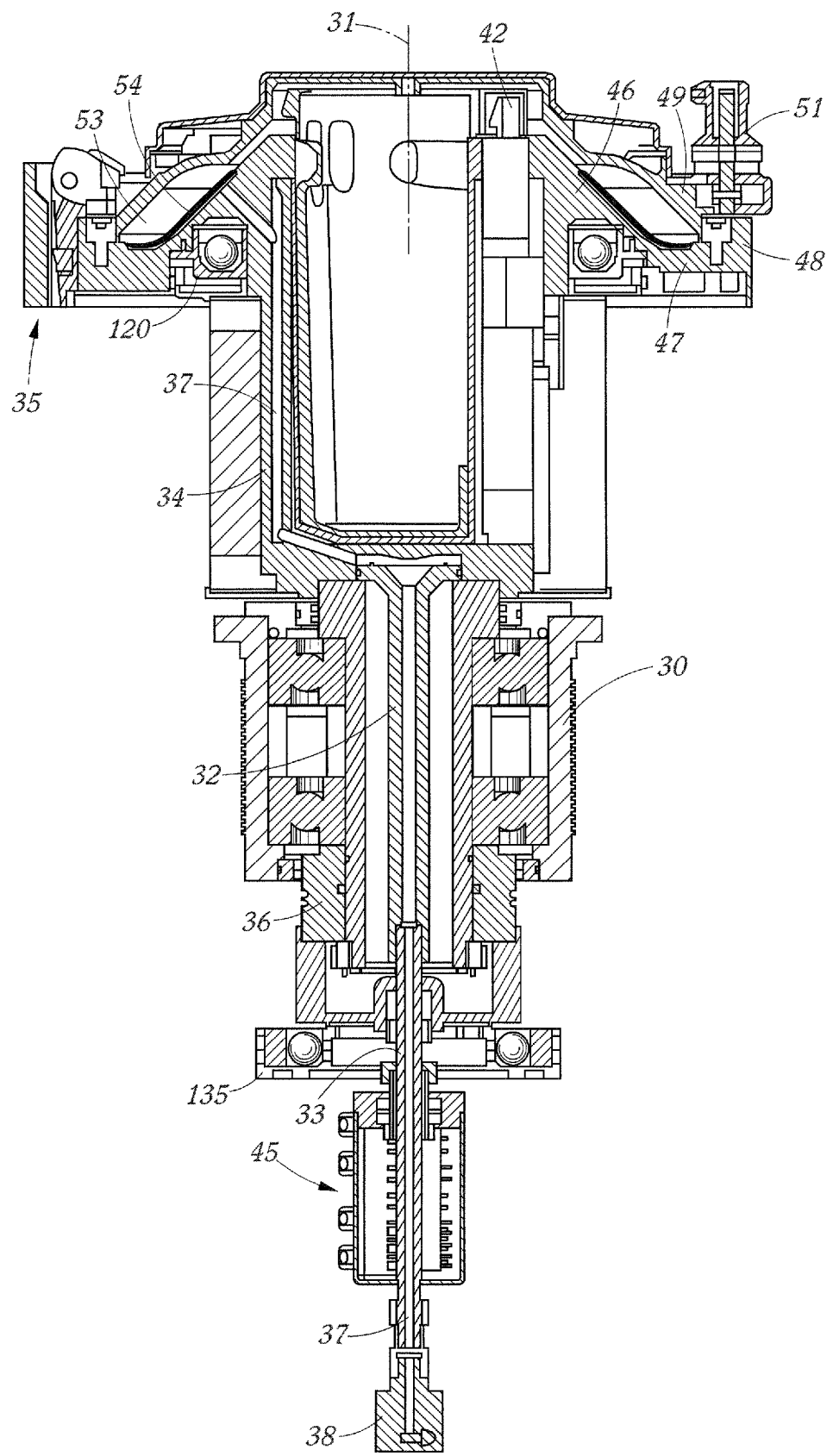
FIG. 4 is a cross-section view, along a diametral plane, of the rotor of a second embodiment of a separation apparatus.

FIGS. 3 and 4 show two embodiments of an apparatus for separating a volume of composite liquid by centrifugation. The apparatus comprises a centrifuge adapted for receiving either set of separation bags shown in FIGS. 1 and 2, and a component transferring means for causing the transfer of separated components into the satellite bags.

The centrifuge comprises a rotor that is supported by a bearing assembly 30 allowing the rotor to rotate about a central axis 31. The rotor comprises: a cylindrical rotor shaft 32, 33; a central container 34 for containing satellite bags, which is connected to the rotor shaft 32, 33 at the upper end thereof; and a circular turntable 35 for supporting a separation bag, which is connected to the container 34 at the upper end thereof, the central axes of the rotor shaft 32, 33, the container 34 and the turntable 35 coinciding with the rotation axis 31. The rotor shaft comprises a first upper portion 32 and a second lower portion 33. The upper portion 32 of the shaft extends in part through the bearing assembly 30. A pulley 36 is connected to the lower end of the upper portion 32 of the shaft. A balancing assembly 120, is secured to the turntable 35. The rotor of FIG. 4 comprises an upper balancing assembly 120 secured to the turntable 35 and a lower balancing assembly 135 (FIG. 4) that is secured to the second lower portion 33 of the rotor shaft.

The centrifuge further comprises a motor 40 coupled to the rotor by a belt 41 engaged in a groove of the pulley 36 so as to rotate the rotor about the central vertical axis 31.

The separation apparatus further comprises a first, second and third pinch valve members 42, 43, 44 (FIGS. 1 and 2) that are mounted on the rotor for selectively blocking or allowing a flow of liquid through a flexible plastic tube, and selectively sealing and cutting a plastic tube. Each pinch valve member 42, 43, 44 comprises an elongated cylindrical body and a head having a groove that is defined by a stationary upper jaw and a lower jaw movable between an open and a closed position, the groove being dimensioned so that one of the transfer tubes 14, 20, 21 of the bag sets shown in FIGS. 1 and 2 can be snuggly engaged therein when the lower jaw is in the open position (see element 42, FIG. 5). The elongated body contains a mechanism for moving the lower jaw and it is connected to a radio frequency generator that supplies the energy necessary for sealing and cutting a plastic tube. The pinch valve members 42, 43, 44 are mounted at the periphery of the central container 34 so that their longitudinal axes are parallel to the central axis 31 of the rotor and their heads protrude above the rim of the container 34. The position of the pinch valve members 42, 43, 44 with respect to the separation bag 1 and the transfer tubes 14, 20, 21 connected thereto when the separation bag 1 is mounted on the turntable 35 is shown in doted lines in FIGS. 1 and 2. Electric power is supplied to the pinch valve members 42, 43, 44 through a slip ring array 45 that is mounted around the lower portion 33 of the rotor shaft.

The turntable 35 comprises a central frusto-conical portion 46, the upper, smaller edge of which is connected to the rim of the container 34, an annular flat portion 47 connected to the lower, larger edge of the frusto-conical portion 46, and an outer cylindrical flange 48 extending upwards from the outer periphery of the annular portion 47. The turntable 35 further comprises a vaulted circular lid 49 that is secured to the flange 48 by a hinge so as to pivot between an open and a closed position. The lid 49 is fitted with a lock 51 by which it can be blocked in the closed position. The lid 49 has an annular interior surface that is so shaped that, when the lid 49 is in the closed position, it defines with the frusto-conical portion 46 and the annular flat portion 47 of the turntable 35 a frusto-conical annular container 53 having a radial cross-section that has substantially the shape of a parallelogram. The frusto-conical annular container 53, later the "separation compartment", is intended for containing the separation bag 1 shown in FIGS. 1 and 2.

The upper balancing assembly 120, which has generally the shape of a ring and will be described in detail later, is mounted on the rotor within the space that extends between the upper end of the central container 34 and the frusto-conical wall 46 of the turntable 35. It results from this arrangement that the upper balancing assembly is located underneath the turntable 35.

In the embodiment of the separation apparatus represented in FIG. 4, the lower balancing assembly 135, which is of the same type as the upper balancing assembly 120, although of lesser diameter, is secured to the second lower part 33 of the rotor shaft underneath the pulley 36 and above the slip ring array 45.

The component transferring system comprises a squeezing system for squeezing the separation bag within the separation compartment 53 and causing the transfer of separated components into the satellite bags. The squeezing system comprises a flexible annular diaphragm 54 that is so shaped as to line the frusto-conical portion 46 and the annular flat portion 47 of the turntable 35, to which it is secured along its smaller and larger circular edges. The squeezing system further comprises a hydraulic pumping station 60 for pumping a hydraulic liquid in and out of an expandable hydraulic chamber 55 defined between the flexible diaphragm 54 and the turntable 35, via a duct 37 extending through the rotor from the lower end of the lower portion 33 of the rotor shaft to the turntable 35. The pumping station 60 comprises a piston pump having a piston 61 movable in a hydraulic cylinder 62 fluidly connected via a rotary fluid coupling 38 to the rotor duct 37. The piston 61 is actuated by a stepper motor 63 that moves a lead screw 64 linked to the piston rod. The hydraulic cylinder 62 is also connected to a hydraulic liquid reservoir 65 having an access controlled by a valve 66 for selectively allowing the introduction or the withdrawal of hydraulic liquid into and from a hydraulic circuit including the hydraulic cylinder 62, the rotor duct 37 and the expandable hydraulic chamber 55. A pressure gauge 67 is connected to the hydraulic circuit for measuring the hydraulic pressure therein.

The separation apparatus further comprises three sensors 56, 57, 58 (FIGS. 1 and 2) for detecting characteristics of the separation process occurring within a separation bag when the apparatus operates. The three sensors 56, 57, 58 are embedded in the lid 49 at different distances from the rotation axis of the rotor, a first sensor 56 being the farthest to the rotation axis, a third sensor 58 being the closest to the rotation axis and a second sensor 57 occupying an intermediate position. When the lid 49 is closed, the three sensors 56, 57, 58 face the separation bag 1 as shown in FIGS. 1 and 2. The first sensor 56 (later the "bag sensor") is embedded in the lid 49 so as to be positioned over the separation chamber 5, at about one third of the width of the separation chamber from the inner edge 6 thereof, and it is offset with respect to the passage 11 between the separation chamber 5 and the distribution channel 10. The bag sensor 56 is able to detect the presence or absence of a liquid in the separation chamber 5, as well as red blood cells in a liquid. The second sensor 57 (later the "bay sensor") is embedded in the lid 49 so as to be positioned over the passage 11 between the separation chamber 5 and the distribution channel 10. The bay sensor 57 is in the pathway of any component flowing from the separation chamber 5 into the three satellite bags 2, 3, 4. The bay sensor 57 is able to detect the presence or absence of a liquid in the distribution channel 10 as well as to detect red blood cells in a liquid. The third sensor 58 (later the "channel sensor") is embedded in the lid 49 so as to be positioned over the distribution channel 10. The channel sensor 58 is in the pathway of any component flowing from the separation chamber 5 into the second satellite bag 3. The channel sensor 58 is able to detect the presence or absence of a liquid in the distribution channel 10 as well as to detect red blood cells in a liquid. Each sensor 56, 57, 58 may comprise a photocell including an infra-red LED and a photo-detector. Electric power is supplied to the sensors 56, 57, 58 through the slip ring array 45.

The separation apparatus further comprises a controller 70 including a control unit (microprocessor) and a memory for providing the microprocessor with information and programmed instructions relative to various separation protocols and to the operation of the apparatus in accordance with such separation protocols. In particular, the microprocessor is programmed for receiving information relative to the centrifugation speed(s) at which the rotor is to be rotated during the various stages of a separation process, and information relative to the various transfer flow rates at which separated components are to be transferred from the separation bag 1 into the satellite bags 2, 3, 4. The information relative to the various transfer flow rates can be expressed, for example, as hydraulic liquid flow rates in the hydraulic circuit, or as rotation speeds of the stepper motor 63 of the hydraulic pumping station 60. The microprocessor is further programmed for receiving, directly or through the memory, information from the pressure gauge 67 and from the photocells 56, 57, 58 and for controlling the centrifuge motor 40, the stepper motor 63, and the pinch valve members 42, 43, 44 so as to cause the separation apparatus to operate along a selected separation protocol.

FIGS. 5 to 8 show an embodiment of a bag vessel 79 designed for fitting within the central container 34 of the rotor of FIGS. 3 and 4. The bag vessel 79 has generally the shape of a bucket having a bottom wall 80, a lateral wall 81 and a flange 82 that extends outwards from the upper rim of the lateral wall 81.

The lateral wall 81 is substantially defined by a frustum of a cone flaring upwards, which is intersected by a flat plane extending in parallel to the axis of the frustum of a cone. The lateral wall 81 has therefore a first portion that is a sector of a frustum of a cone, connected to a second portion that is flat and has the shape of a parallelogram. The axis of the frustum of a cone partially defining the first portion of the lateral wall 81 coincides with the rotation axis 31 of the rotor. The angle of the frustum of a cone is about 3 degrees. It could be more open, however, the larger the angle, the smaller the space available inside the container for storing the satellite bags.

The flange 82 is annular and has the shape of a frustum of a cone having an angle of about 85 degrees. A series of rounded pins 83 arranged on a circle protrude upwards from the flange 82. The size and the location of the pins 83 correspond to the size and location of the holes 12 in the semi-flexible disk-shaped connecting element 9 of a separation bag 1. The pins help position the separation bag 1 on the rotor, and prevent the separation bag 1 from moving with respect to the rotor when the rotor is rotating. Along the flat portion of the lateral wall 81 of the container, the flange 82 comprises three aligned circular apertures 84, 85, 86 that encroach in part on the adjacent flat wall. In the assembled state of the rotor, the three pinch valve members 42, 43, 44 extend through the apertures 84, 85, 86, so that the heads of the pinch valve members protrude above the flange 82.

The bag vessel 79 comprises a support member for receiving at least one satellite bag full of a liquid and holding it in such a way that the content of the satellite bag is fully transferred into a separation bag connected to the satellite bag when the rotor is rotated at a selected speed. The support member is generally arranged so that a satellite bag received therein has a lower portion that is closer to the rotation axis 31 of the rotor that an upper portion thereof to which a transfer tube is connected.

The support member generally comprises: a portion of wall that is tilted with respect to the rotation axis 31 of the rotor; a securing apparatus for securing the upper part of a satellite bag to an upper part of the tilted wall so that a satellite bag containing a liquid that is secured to the tilted wall by the securing apparatus bears against the tilted wall, with a lower portion of the satellite bag that is closer to the axis of rotation than an upper portion thereof.

In the embodiment represented in the FIGS. 5 to 8, the support member comprises a cradle 87, which forms a removable part of the bag vessel 79, and a bag holder 100 by which several satellite bags can removably be secured to the cradle 87 so as to occupy a determined position within the bag vessel 79.

The cradle 87 has a first outer lateral wall 88, which extends over the height of the bag vessel 79, and a second inner lateral wall 89, which extends from the bottom of the cradle over about one third of the eighth of the bag vessel 79. The first outer lateral wall 88 is a sub-sector of the sector of frusto-conical wall that forms the first portion of the lateral wall 81 of the bag vessel 79. As mentioned above, the angle of this sector of frusto-conical wall is about 3 degrees. The second inner lateral wall 89 is a sector of a cylinder having a longitudinal axis parallel to the rotation axis 31 of the rotor. The concavity of the second inner lateral wall 89 faces the first outer lateral wall 88 of the cradle 87. The cradle 87 further comprises a bottom wall having a flat portion 90, perpendicular to the axis of rotation 31 of the rotor, which is connected to the lower rim of the second inner lateral wall 89 (sector of cylinder) and a curved portion 91, which raises from the flat portion 90 to a point located on a median longitudinal axis of the first outer lateral wall 88 (sector of frustum of a cone), at about one fifth of the height of the cradle 87, from the flat bottom portion 90. In geometrical terms, the second portion 91 of the bottom of the cradle 87 results from the intersection of a frustum of a cone and of a cylinder having perpendicular axes.

The cradle 87 further comprises two lateral recesses 92 opening in its upper part, at the same level, on its inner surface, for removably receiving and locking the ends of complementary locking elements of a bag holder to be described later. A guide 93, in the form of a narrow tongue, extends from the bottom of each recess 93 towards the lateral edges of the cradle 87 for helping set the bag holder in place. Between the two locking recesses 92 the cradle 87 comprises two other recesses 94, 95 for accommodating the end of the transfer tubes connected to the satellites bags.

As a removable part of the bag vessel 79, the cradle 87 performs a second function, besides enabling the transfer, under centrifugation forces, of the content of a bag secured thereto to the periphery of a rotor. This second function is a loading function, which, in particular, makes it possible for an operator having two cradles at his disposal to install a second set of bags in a second cradle when a first cradle supporting a first set of bags is spun in a centrifuge, and to load the second cradle in the centrifuge as soon as the first cradle has been removed therefrom after the content of the first set of bags has been processed.

The support member for receiving at least one satellite bag within the bag vessel 79 and holding it in a determined position further comprises a bag holder 100, which has two main functions. First, it is used during the manufacture and shipping of the bag sets represented in FIGS. 1 and 2 to help assemble the bags together and keep them in a fixed position with respect to each other during sterilization and shipping so that the transfer tubes form large loops and do not kink. Second, the bag holder 100 is used for securing the satellite bags 2, 3, 4 to the cradle 87 in a determined position during the operation of the centrifuge.

Figure 9:
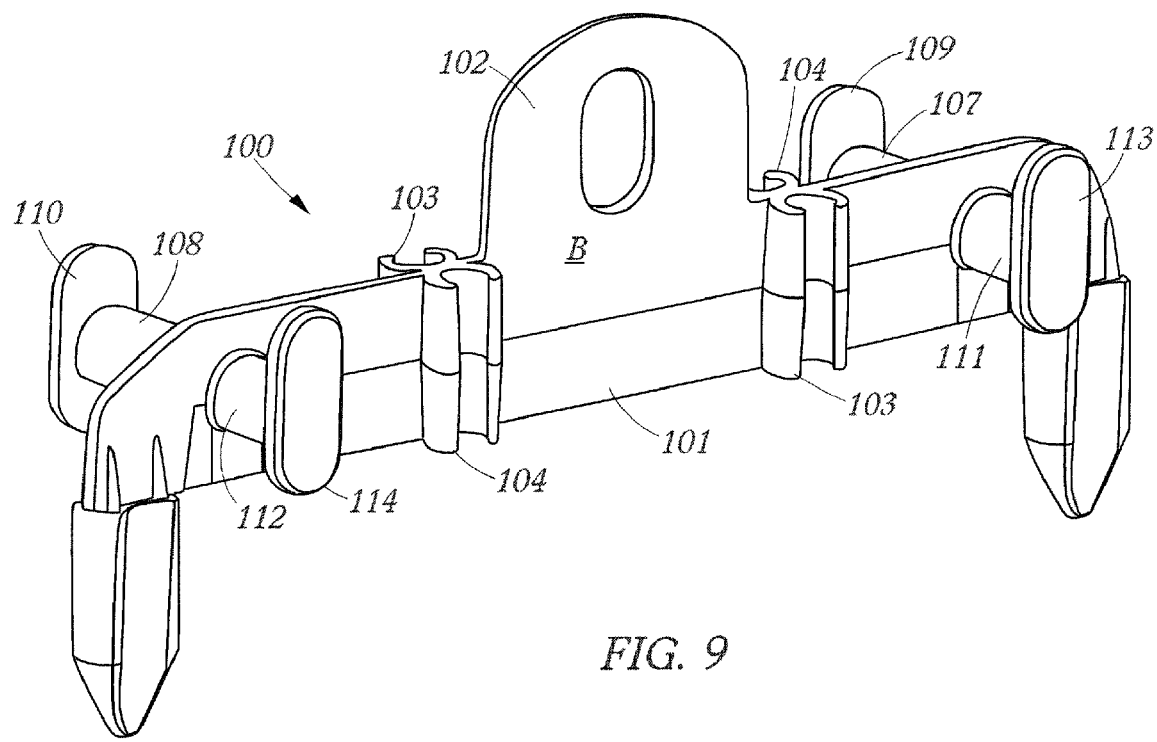
FIGS. 9 and 10 are perspective views of a bag holder fitting in the bag cradle of FIGS. 6 to 8.
Figure 10:
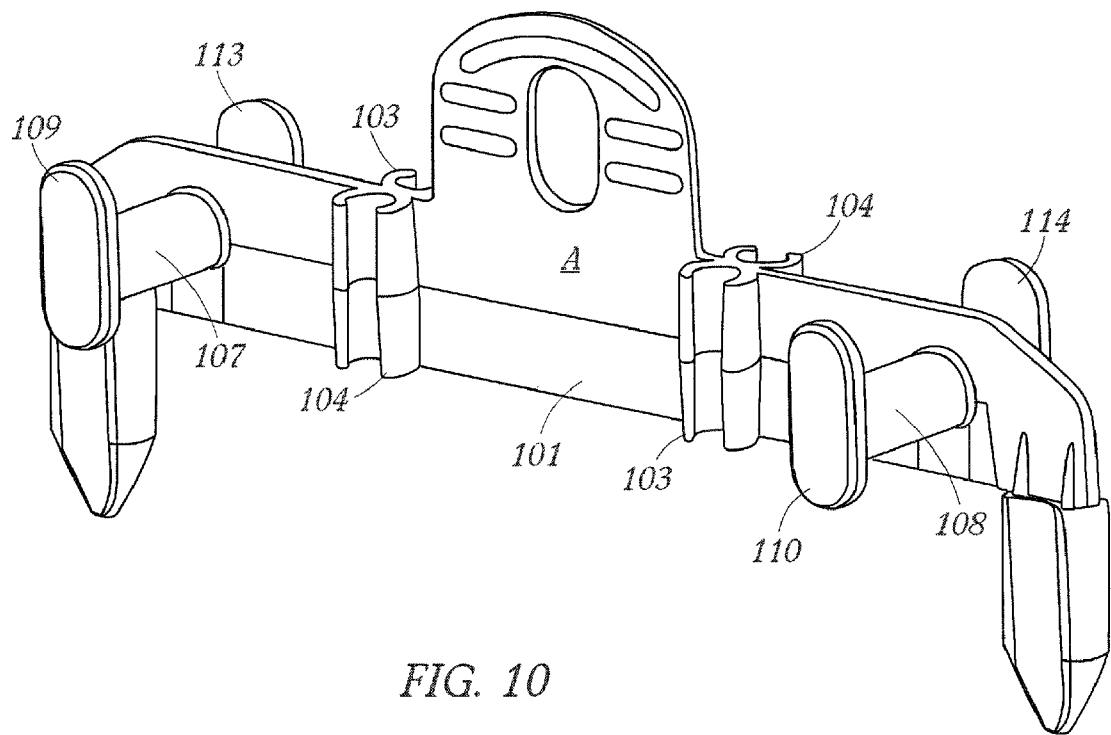

FIGS. 9 and 10 represent the two sides A and B of a bag holder 100. The bag-holder 100 comprises an elongated flat body 101 in the middle of which a flat U-shaped handling appendage 102 is connected so as to protrude upwards when the bag-holder 100 is mounted in the cradle 87. The elongated flat body 101 is fitted on both sides A and B with two parallel gutter-like guides 103, 104 that are perpendicular to a longitudinal axis of the elongated flat body 101 and extend in a central portion of the elongated flat body 101, substantially in alignment with the lateral edges of the U-shaped handling appendage 102, respectively. When the bag holder 100 is secured to the cradle 87, the elongated flat body 101 is substantially perpendicular and the gutter-like guides 103, 104 are substantially parallel to the rotation axis 31 of the rotor. The gutter-like guides 103, 104 are so dimensioned that a portion of transfer tube 14, 20, 21 or a needle sheath 18 can be snuggly engaged therein.

The bag-holder 100 further comprises a hanger in the form of a first couple of pegs 107, 108 connected to the elongated flat body 101 for hanging at least one satellite bag 2, 3, 4 in the cradle 87. The pegs 107, 108 extend perpendicularly from the side A of the elongated flat body 101. The distance between the two pegs 107, 108 is substantially the same as the distance between the holes 13 in the ears of the satellite bags 2, 3, 4. The cross-section of the pegs 107, 108 substantially fits in the holes 14.

The pegs 107, 108 are also used to secure the bag holder 100 to the cradle 87. To this end, the distance between the two pegs 107, 108 is substantially the same as the distance between the two locking recesses 92 in the upper part of the cradle 87. Also, the tip of each peg 107, 108 is fitted with a locking element 109, 110 that can removably lock within a locking recess 92 of the cradle 87. Each locking element 109, 110 is comprised of a plate having rounded ends, which is perpendicularly connected to the corresponding pegs 107, 108.

The bag-holder 100 further comprises a second couple of pegs 111, 112 connected to the elongated flat body 101 for releasably securing a separation bag 1 and, a the case may be, a satellite bag 2, 3, 4 thereto. The pegs 111, 112 extend perpendicularly from the side B of the elongated flat body 101 along the same axis as the pegs 107, 108. The tips of the pegs 111, 112 are fitted with retaining elements 113, 114 for preventing a satellite bag engaged on the pegs from escaping therefrom during centrifugation of the bag assembly. Overall, the second couple of pegs 111, 112 is identical to the first couple of pegs 107, 108 save for the length of the pegs, which is longer in the first couple than in the second couple.

It results from the respective arrangement of the elongated flat body 101 and the first and second couple of pegs 106, 107, 111, 112 that product bags 2, 3, 4 engaged on the pegs occupy a determined position in the central container of a rotor when the cradle 87 is assembled to the remaining part of the bag vessel 79. Moreover, when the rotor start rotating, a satellite bag full of liquid mounted in the cradle 87 by means of the first couple of pegs 107, 108 is stuck by centrifugation forces or g-forces onto the frusto-conical wall 88 and the rounded bottom part 91 of the cradle 87 so that the upper part of the bag is farther apart from the rotation axis 31 of the rotor than the lower part of the bag. Thanks to this disposition, when the transfer tube connecting the satellite bag to the separation bag is open and the rotation speed is high enough, the liquid initially contained in the satellite bag wholly drains into the separation bag.

Figure 5:
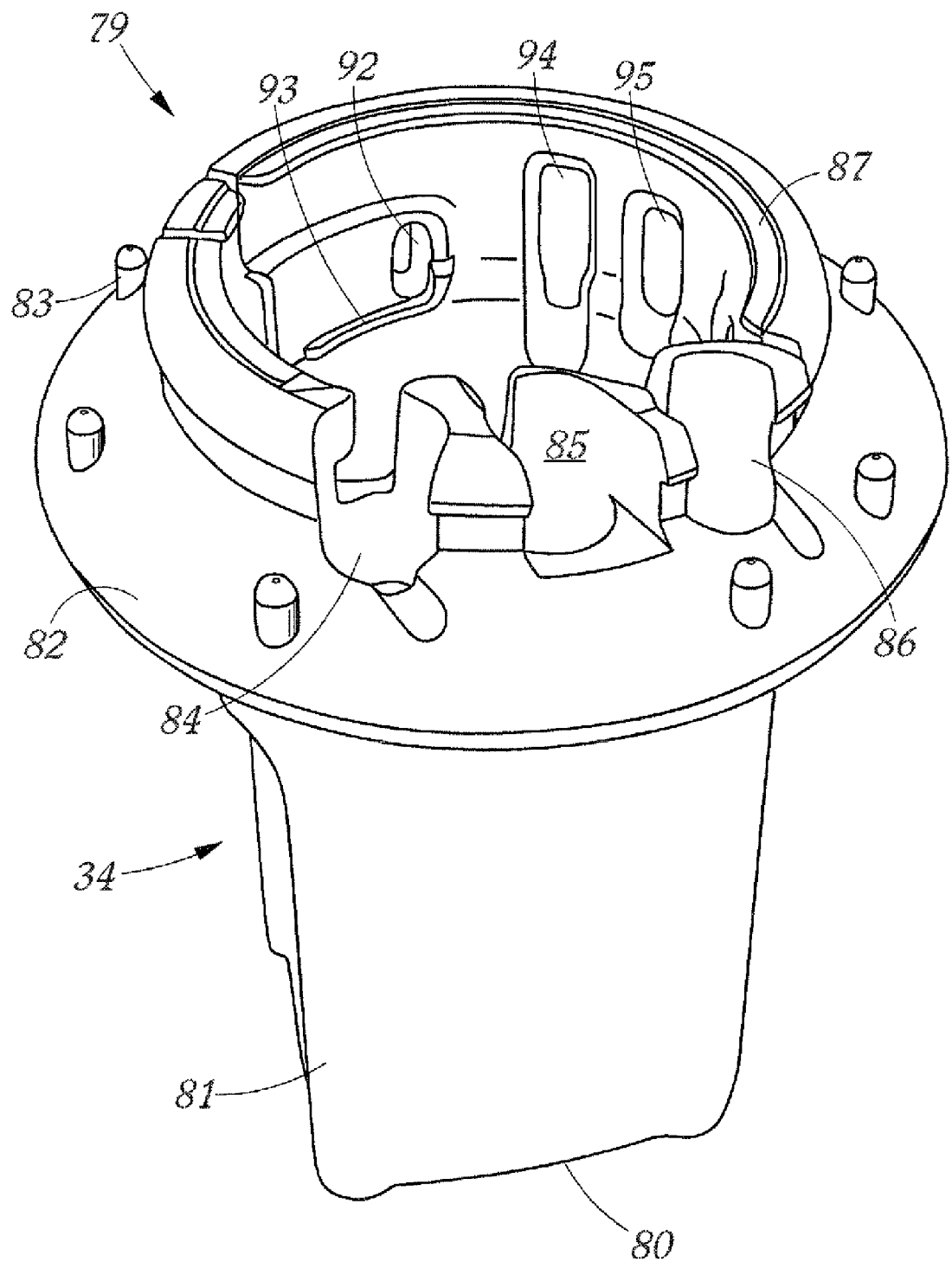
FIG. 5 is a perspective view of an embodiment of a bag vessel fitting within a rotor of a separation apparatus.
Figure 6:
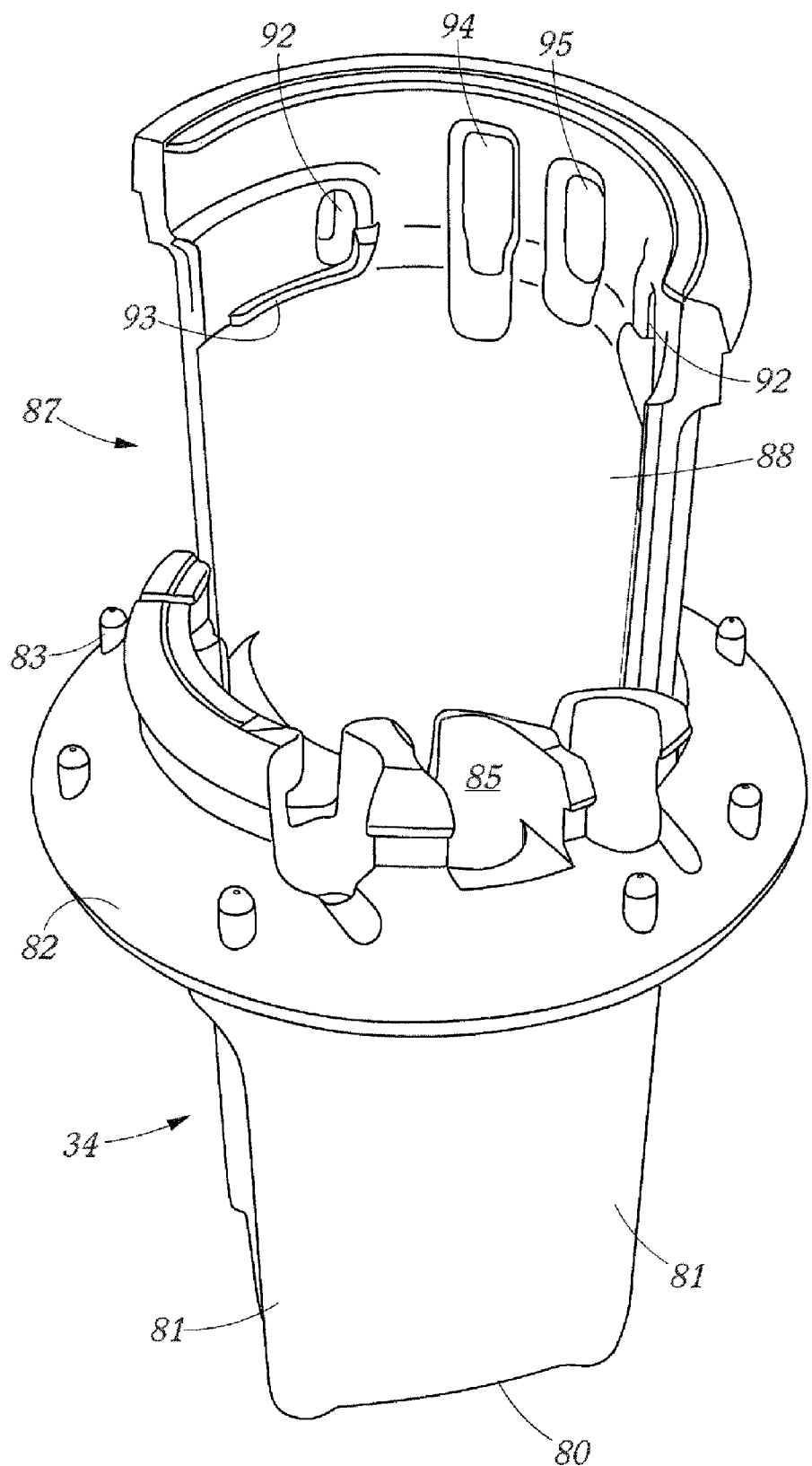
FIG. 6 is a perspective view of the bag vessel of FIG. 4, in which a bag cradle is shown partially withdrawn.

Variants of the upper part of the rotor described above, are as follows: the bag vessel 79 can be an integral part of the rotor or it can be a removable liner fitting within a central compartment of the rotor; the cradle 87, instead of being a removable part of the bag vessel 79, can be integral with the rest of the bag vessel 79; the cradle 87, instead of being a removable part of the bag vessel 79, can be a movable part thereof that can be lifted from a lower position (as shown in FIG. 5) to an upper position (as represented in FIG. 6) making it easy to load and unload a set of bags; the internal surface of the cradle 87 onto which a satellite bag full of liquid is stuck by centrifugal forces when the rotor is rotated can be substantially flat and tilted at an angle with respect to the rotation axis of the rotor allowing for a complete drainage of the satellite bag when the rotor is rotated; the cradle 87 can be fitted with two spaced apart pegs protruding inwards from an upper part thereof. These alternative pegs would be used to hang the satellite bags within the rotor instead of using the bag holder 100.

The various elements of the rotor described above are so designed and assembled that the rotor proper is balanced, or, in other words, the weight of its various components is equally distributed with respect to the axis of rotation of the rotor.

However, the operation of the above separation apparatus, as illustrated in the two examples of separation protocols that are described below, causes an unbalance of the rotor, which is variable and can last for a fraction of a separation process or for the whole separation process. When the separation bag used is ring-shaped, like in FIGS. 1 and 2, the unbalance does not take place in the separation bag, at the periphery of the rotor, but only in the satellite bags, which are placed in the central container 34 at a short distance from the rotation axis 31 of the rotor. An unbalance of the rotor can be generated during a separation process, for example, when a separated component is transferred from a separation bag into a satellite bag. It can also be generated before the beginning of a separation process when a satellite bag containing a volume of liquid (e.g. whole blood or a cell washing solution) is placed in the central container of the rotor, and the liquid is transferred into a separation bag during centrifugation (either the whole volume at the beginning of the separation process, or the whole volume at one point in time during the separation process, or two or more parts of the volume at time intervals). Typically, an inbalance occurs when a volume of liquid is transferred.

A characteristic of the unbalance of the rotor that occurs during a separation process performed by the above separation apparatus is that it is an unbalance that has no fixed value and center of gravity: it is an unbalance that varies when the weight of a satellite bag increases or decreases, and the center of gravity changes or goes down during the transfer of a liquid from the separation bag into the satellite bag.

The unbalance of the rotor of such a separation apparatus is generally undesirable because it causes noise and vibrations, the latter causing in turn a rapid wear as well as a possible loosening of certain rotating parts.

In order to neutralize the variable unbalance that is generated at various points in time during operation of the above separation apparatus, it is fitted with a balancing apparatus adapted to counterbalance any volume of liquid stored permanently or transiently in the central container 34 of the rotor.

The balancing apparatus of the separation apparatus comprises one (see FIG. 3) or two (see FIG. 4) balancing assemblies (120, 135), each including a series of ponderous satellites that can move freely on a specific circular orbit centered on and perpendicular to the axis of rotation of the rotor.

The weight of the ponderous satellite, the number of the satellites, and the diameter of the orbit on which the satellites are free to revolve are selected in view of 1) an anticipated maximum unbalance to be neutralized, 2) the distance from the axis of the rotor where the cause of the unbalance is to occur and 3) the space that is available on the rotor for mounting the balancing assembly.

Figure 11:
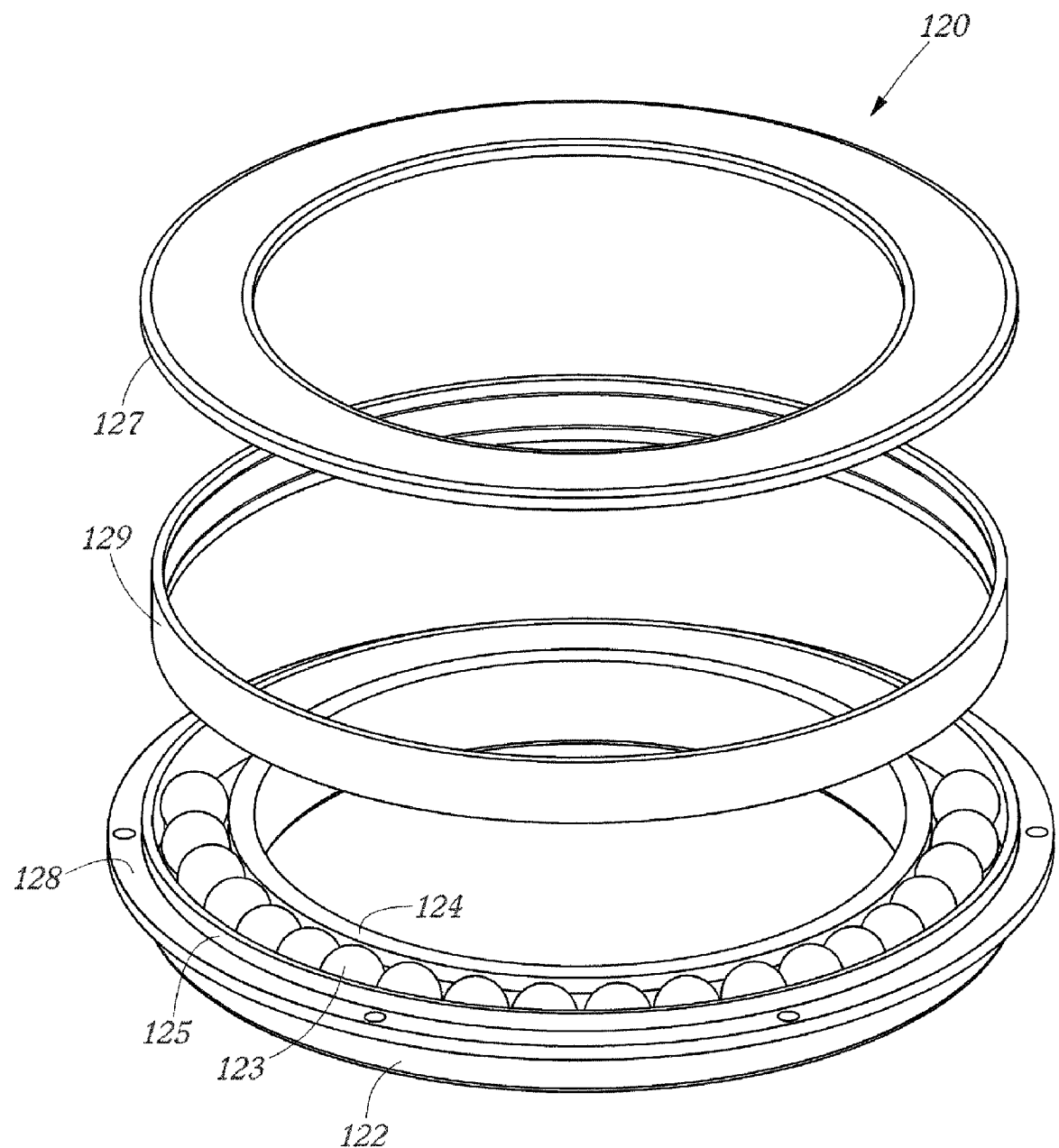
FIG. 11 is a perspective exploded view of a first embodiment of a balancing assembly for a separation apparatus.
Figure 12:
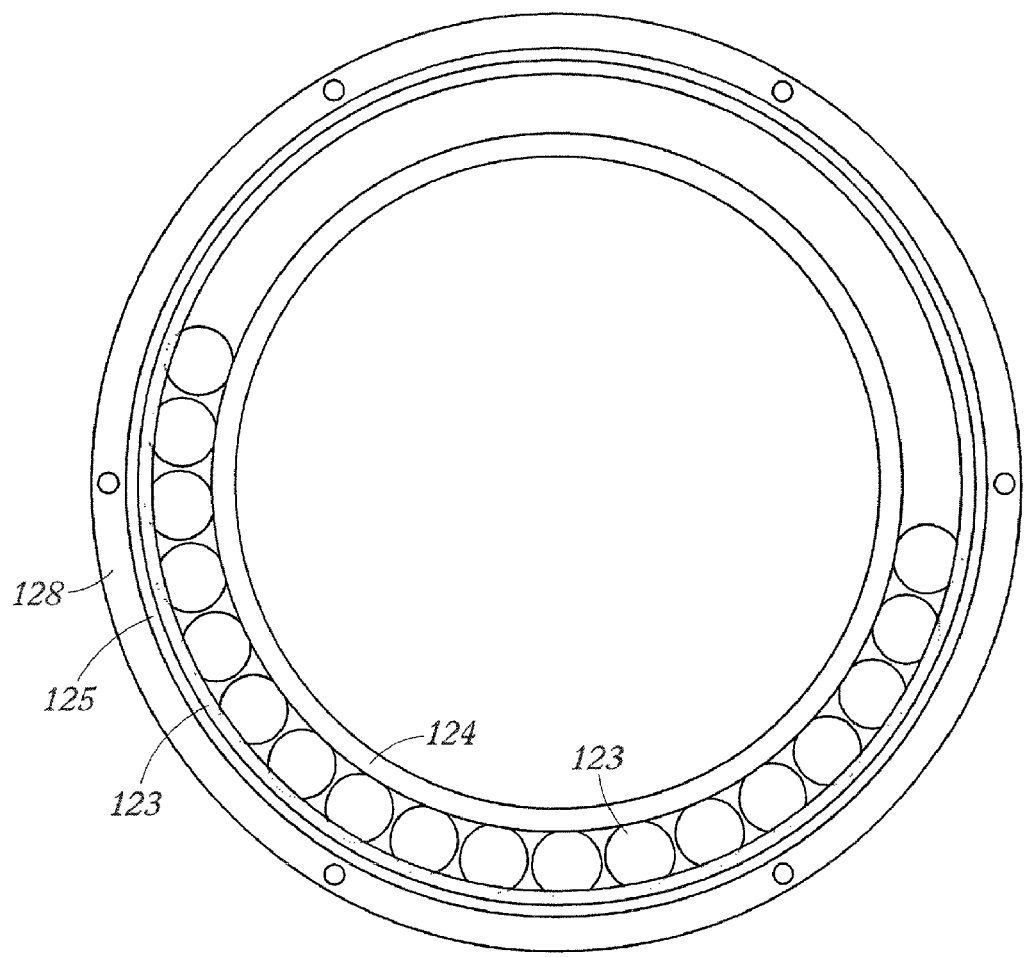
FIG. 12 is a top view of the balancing assembly of FIG. 11.
Figure 13:
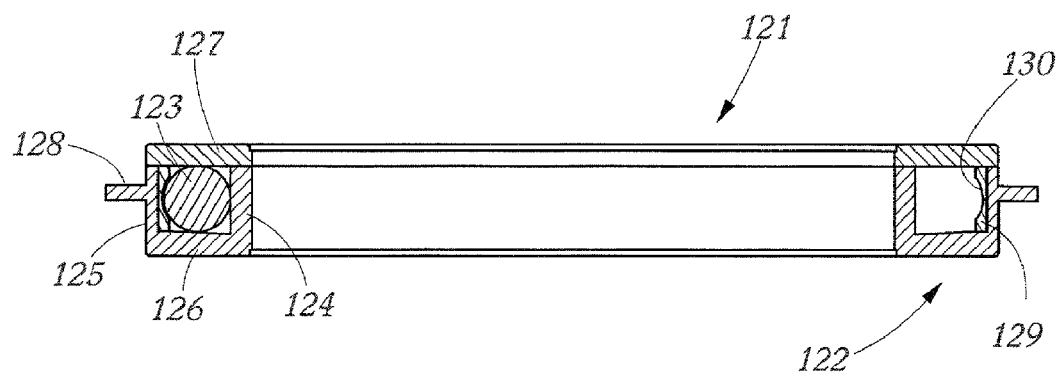
FIG. 13 is a cross-section, along a diametral plane, of the balancing assembly of FIGS. 11 and 12.

FIGS. 11 to 13 show a first embodiment of a balancing assembly 120 that is adapted to the above separation apparatus. The balancing assembly 120 comprises a ring-shaped housing 121 defining a cavity whose cross-section, along a radial plane, is generally rectangular. The housing 121 comprises a container 122 for spherical ponderous satellites (balls) 123, which cross-section along a radial plane is generally U-shaped. The container 122 has an inner and outer cylindrical walls 124, 125, which are concentric, and a bottom wall 126 that joins the inner and outer walls 124, 125 and has therefore the shape of a flat ring. The housing 121 further comprises a cover 127, having the shape of a flat ring, for closing the container 122.

The balancing assembly 120 further comprises a connecting member 128 for its connection to the rotor. The connecting member 128 has the shape of a circular shoulder protruding from the outer side of the outer wall 125 of the container 122.

The balancing assembly 120 further comprises a cylindrical outer race 129, having an outer diameter substantially equal to the inner diameter of the outer wall 125 of the container 122 so as to snugly fit within the container 122. The race 129 comprises on its inner side a shallow circular recess 130 in which the balls 123 slightly engage, and on which they roll, when the rotor rotates.

The balancing assembly 120 comprises a plurality of balls 123 having a diameter that is slightly less than the radial depth of the cavity of the housing 122. When the balls 123 are in contact with each other, as shown in FIGS. 11 and 12, they occupy a sector of the container 122 of about 180 degrees.

The balancing assembly 120 also comprises a damper or dampening fluid or element for providing resistance to the movement of the balls 123 in the housing 122 and for dampening any noise caused by the balls 123 coming into contact with each other during the operation of the separation apparatus. The dampening fluid comprises a liquid of determined viscosity that partially fills the container 122. The liquid is also selected for not having any corroding effect on the materials of which the housing 122, the race 129 and the balls 123 are made, and for not deteriorating in the normal operating conditions of a separation apparatus.

In one embodiment of the balancing assembly 120 (135), the housing 121 (container 122 and cover 127) is made of aluminum, the race 129 is made of hardened steel as well as the balls 123. The dimensions of the upper balancing assembly 120 are as follows: the outer diameter of the housing 121 is about 265 mm, and the height and width of the radial cross section of the housing 121 are about 30×30 mm. The upper balancing assembly 120 comprises eighteen balls whose diameter is about 19 mm. The dampening fluid comprises about 90 ml of synthetic oil having a viscosity of about 350 cst. The balancing capacity of the upper balancing assembly 120 is about 33000 gmm.

In one embodiment of the lower balancing assembly 135, the outer diameter of the housing is about 168 mm and the height and width of the radial cross section of the housing 121 are about 25×25 mm. The lower balancing assembly 135 comprises eleven balls whose diameter is about 18 mm. The dampening fluid comprises about 40 ml of synthetic oil having a viscosity of about 350 cst. The balancing capacity of the lower balancing assembly 135 is about 8000 gmm.

Figure 14:
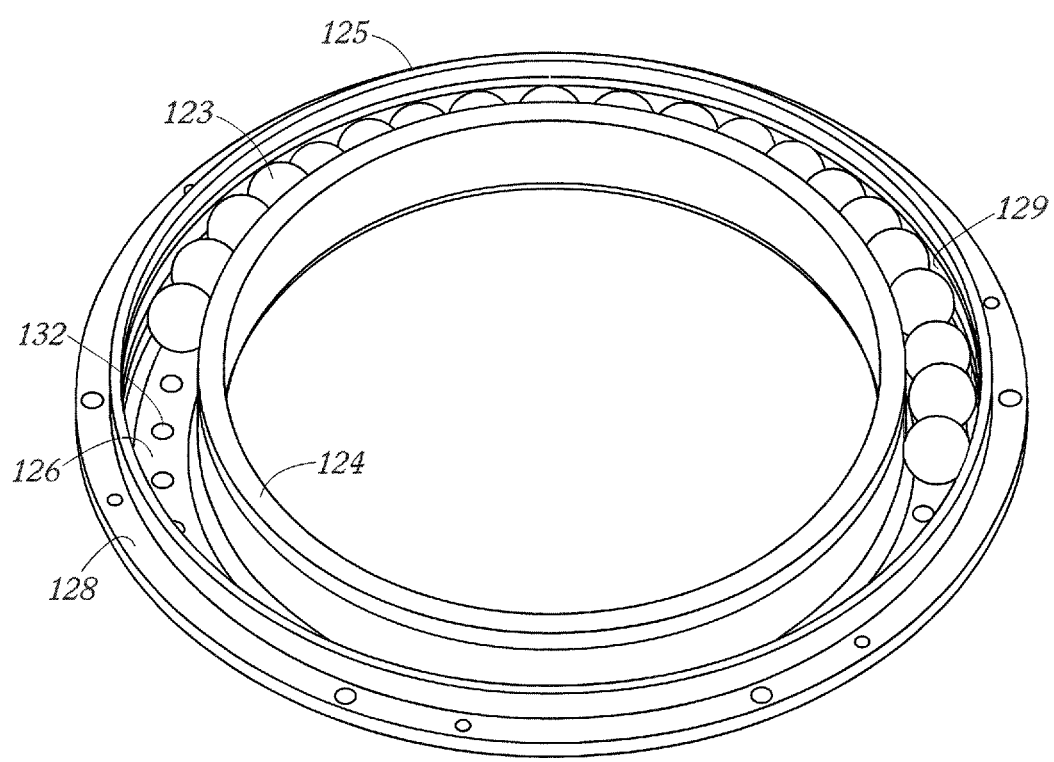
FIG. 14 is a perspective view of the lower part of a second embodiment of a balancing assembly for a separation apparatus.

FIG. 14 shows a second embodiment of a balancing assembly for a separation apparatus. This second embodiment differs from the embodiment shown in FIGS. 11 to 13 in that it comprises temporary stopping or parking structure or elements 132 for preventing the balls 123 from moving more than a short predetermined distance within the housing 121 when the balancing assembly is inclined with respect to a horizontal plane of an angle that is less than a predetermined angle, while allowing the balls 123 to move freely when the rotor is rotating at a speed that is above a determined value.

A purpose of stopping or parking structure 132 is to prevent the balls from gathering one against the other around a lower point of the balancing assembly 120 when the separation apparatus is uneven or tilted. This unevenness can be caused by uneven ground, or uneven support. Any unevenness that causes the balancing assembly to be tilted with respect to an horizontal plane may cause the balls to gather one against the other. In other words, if the separation apparatus is not used for a period of time while on uneven ground, each ball 123 will move in the direction of the lower point of the balancing assembly 120 until it is stopped by the closest stopping or parking structure or element 132. The next time the separation apparatus is started, the balls 123 will be distributed around the rotor more or less the way they were during the end stage of the last use of the apparatus, and their displacement towards their new balancing position will be minimal. This also ensures a more even distribution of the balls for machine start.

In the embodiment shown in FIG. 14, the stopping or parking structure or element comprises a plurality of conic dents 132 within the bottom wall 126 of the housing 121. The number of dents 132 is twice the number of balls 123, namely thirty-six, evenly distributed on a circle that is substantially equidistant from the inner and outer walls 124, 125 of the housing 122. The diameter of the base of each dent 132 is 6 mm. A ball 123 engaged in a dent 132 will stay so unless the balancing assembly 120 is inclined more that 18 degrees with respect to an horizontal plane. When the rotation speed of the rotor exceeds a predetermined rotation speed or the g-force exceeds a pre-determined force, the balls 123 escape the dents 132 and move under centrifugation forces into the circular recess 130 in the race 129, which is then the only surface they contact in the housing 121.

As mentioned above, FIGS. 3 and 4 show a first and second embodiments of a separation apparatus that differ from each other in that the balancing apparatus of the first embodiment (FIG. 3) comprises an upper balancing assembly 120 secured to the rotor underneath the turntable 35, and the balancing device of the second embodiment (FIG. 4) comprises, in addition to an upper balancing assembly 120, a lower balancing assembly 135 that is secured to the rotor shaft 33, between the pulley 36 and the slip ring array 45.

The selection of a balancing apparatus comprising one or two balancing assemblies is made depending on the following considerations.

First, depending on the use of the separation apparatus, the unbalance caused in the rotor can vary substantially: for example, a separation protocol may comprise loading in the central compartment of the rotor a whole blood collection bag (about 500 ml) the content of which is to be transferred during rotation of the rotor into a separation bag. In another separation protocol, the volume of whole blood to be separated is transferred by gravity into the separation bag before the beginning of the separation process, and the rotor is therefore not initially unbalanced. In this case, the rotor will become unbalanced later when a plasma component and, as the case may be, a platelet or other blood component is transferred into the central compartment of the rotor (about 200-300 ml, depending on the hematocrit). When implementing the first protocol, more balancing capacities are needed than when implementing the second protocol if the rotor is to be properly balanced at any time. When, for structural reason, it is not possible to design an upper balancing assembly having increased balancing capacities, that is also generally bulkier, then fitting the separation apparatus with an additional lower balancing assembly is a solution.

Second, in order to balance a rotor in the most appropriate way, the balancing effect should take place at the same level as the center of gravity of the weight causing the unbalance. In the separation apparatuses described above, this is not possible because the filling or the emptying of the satellite bags that takes place during a separation process entails a shift of the center of gravity of the satellite bags. Also, it is desirable that a separation apparatus can perform different separation processes in which the maximum weights of the satellite bags in the central container 34 of the rotor are substantially different. The use of a lower balancing assembly 135 can help fine tune the balancing effect of an upper balancing assembly 120, even when the upper balancing assembly has the balancing capacity required for various separation protocols.

Third, adding a lower balancing assembly may be beneficial from a manufacturing point of view as well as from a servicing point of view. At the end of the manufacturing process, the rotor of a centrifuge must be accurately balanced and this generally entails some fine adjustment work. An additional balancing assembly will compensate for less strict manufacturing tolerances. Also, when an element of the rotor of a centrifuge has to be changed, the rotor must be checked for unbalance, and, as the case may be, be tuned if the new element does not have exactly the same weight as the old one, and/or is not secured to the rotor at exactly the same place. By fitting the rotor with a lower balancing assembly, the tuning of the rotor for neutralizing any unbalance will be easier, if needed at all.

Variants of the balancing assembly, are as follows: It has been already mentioned that the balancing assembly should be dimensioned in view of the maximum unbalance to which the rotor may be subjected, whatever the separation process performed by the separation apparatus. Starting from this specification, the dimension of the balls 123, the number of the balls 123, and the dimensions of the housing 122 can be selected fairly freely in view of the space available on the rotor for mounting the balancing assembly: the bigger the balls, the less the number of balls, the bulkier the housing. However, in order that the balancing assembly provides an optimal balancing, the number of balls should be selected so as to fill a sector of the housing 122 between about 90 degrees and about 270 degrees. Naturally, the separation apparatus would work properly if the balancing capacities of the balancing assembly would exceed the maximum unbalance that can be caused during a separation process. However, such balancing assembly would be heavier, which would increase the inertia of the rotor as well as the amount of energy needed to power it. The ponderous satellites 123, could have any shape (e.g. cylindrical) other than spherical, provided they are designed to freely move in a circular housing under centrifugation forces. The damper or dampening element could comprise a coating on the balls 123 of a hard synthetic material that would generate some friction when the balls are rolling in the housing 121 and limit the noise made by two balls 123 getting in contact with each other. Instead of synthetic oil, any liquid (e.g. silicone oil) having a viscosity between about 200 cst and about 700 cst could be used as dampening fluid, provided that this liquid does not deteriorate in the conditions it will be subjected to in a separation apparatus. The higher the viscosity, the less the amplitude of the move of the rotor at the resonance frequency (run up displacement), but also the less accurate the balancing. For example, synthetic oil commercialized under the trade name Castrol Tribol 800/320 can be used. In the embodiment described above, the volume of synthetic oil used as dampening fluid fills about a half of the housing 121, with the balls 123 being in the housing. The balancing unit would also properly work if the volume of dampening liquid would fill between about 10% and 90% of the housing. The optimal volume of hydraulic liquid within the housing 121 is to be selected as a function of the viscosity of the hydraulic liquid. The higher the viscosity, the less the volume of dampening liquid, and conversely. In the embodiment of FIG. 14, the stopping element comprise twice as many dents 132 as the number of balls 123. The number of dents 132 is selected so as to define a maximum distance that a ball 123 can cover when it rolls on the bottom wall 126 of the housing 121. Since the purpose of the dents is to immobilize the balls at the end of a separation process in a position corresponding approximately to the position they occupied in the housing during the last steady stage (i.e. with a constant rotation speed) of the process, the number of stopping elements could be more and it could be less, but preferably not less than about the number of the balls 123. Instead of dents 132, the stopping elements could comprise protruding elements, like conic bumps or radial ridges protruding from the bottom wall 126. The protruding elements could also be elastic fins protruding from the inner wall 124 so as to partially extend in the housing. An interest of the conic dents described above, besides being easy to manufacture, is that they allow for a compact housing, whereas protruding elements would require that the height (or width) of the housing be increased to allow the balls 123 to roll on the race 129 during centrifugation.

An example of a first separation protocol aiming at the preparation of three blood components, namely a plasma component essentially comprising plasma, a first blood cell component essentially comprising mononuclear cells and platelets, and a second blood cell component essentially comprising red blood cells, is explained below. This first separation protocol does not require the use of the channel sensor 58. The operation of the separation apparatus along the first separation protocol is as follows:

First stage (first protocol): a bag set as shown in FIG. 1, in which a satellite bag contains a volume of whole blood, is set in place in the rotor of a centrifuge (as shown in FIGS. 3, 4).

At the onset of the first stage, the first satellite bag 2 of the bag set of FIG. 1 contains a volume of anti-coagulated whole blood (usually about 500 ml). The collection tube 17 has been sealed and cut. The clamps 15 on the transfer tubes 14, 20, 21 connecting the satellite bag 2, 3, 4 to the separation bag 1 are closed. The frangible pin 16 blocking communication between the first satellite bag 2 and the separation bag 1 is broken as well as the frangible pin 23 blocking communication between the third satellite bag 4 and the separation bag 1. The first satellite bag 2 and the third satellite bags 4 are engaged on the first couple of pegs 107, 108 of a bag holder 100, the first satellite bag 2 being engaged first. The second satellite bag 3 is engaged on the second couple of pegs 111, 112. The bag holder 100 is mounted in a cradle 87 (as shown in FIGS. 6, 7 and 8), as a result of which the first satellite bag 2 is adjacent to the inner surface of the cradle 87. The cradle 87 is inserted into the central compartment 34 of the centrifuge so as to fit with the remaining part of the bag vessel 79. The collection bag 1 is laid on the turntable 35 and the pins 83 on the flange 82 of the bag vessel 79 are engaged in the holes 12 of the disk-shaped connecting element 9 of the separation bag 1. The first transfer tube 14 connecting the first satellite bag 2 to the separation bag 1 is engaged in the first pinch valve member 42, the second transfer tube 20 connecting the second satellite bag 3 to the separation bag 1 is engaged in the third pinch valve member 44, and the third transfer tube 21 connecting the third satellite bag 4 to the separation bag 1 is engaged in the second pinch valve member 43. The clamps 15 on the transfer tubes 14, 20, 21 connecting the satellite bags 2, 3, 4 to the separation bag 1 are opened. The lid 49 of the rotor is closed.

Second stage (first protocol): the anti-coagulated whole blood contained in the first satellite bag 2 is transferred into the separation bag 1.

At the onset of the second stage, the first pinch valve member 42 is open and the second and third pinch valve members 43, 44 are closed. The rotor is set in motion by the centrifuge motor 40 and its rotation speed increases steadily until it reaches a first centrifugation speed (e.g. about 1500 RPM) that is so selected as: to be high enough to cause the transfer, under centrifugation forces, of the content of the first satellite bag 2 into the separation bag 1; to be high enough to cause the whole transfer to happen in the shorter period of time; while, at the same time, to be low enough not to cause pressure within the first satellite bag 2 to substantially exceed a determined pressure threshold above which hemolysis would occur; and to be low enough not to generate shearing forces in the flow of blood entering the separation bag 1 that would cause hemolysis.

It has been determined that the pressure threshold above which hemolysis occurs in the satellite bag 2 is about 10 PSI, and that the maximum rotation speed at which such pressure threshold is not reached and the shearing forces in the blood flow entering the separation bag do not cause hemolysis is about 1800 RPM. At a rotation speed of about 1500 RPM, it takes about one minute for transferring about 500 ml of anti-coagulated blood from the satellite bag 2 into the separation bag 1.

At the onset of the second stage, if the separation apparatus is fitted with a balancing assembly 120 of the type shown in FIGS. 11 to 13 (which does not include stopping elements 132), the balls 123 within the housing 121 occupy whatever positions. In particular, if the separation apparatus stands on uneven ground, the balls 123 are all stuck against each other around the lower point of the balancing assembly 120 (or balancing assemblies 120, 140, if the separation apparatus used is the apparatus shown in FIG. 4). When the rotor starts rotating, the balls 123 move in an inordinate manner until the speed of the rotor exceeds a critical speed that coincides with the resonance frequency of the rigid body modes of the rotor. The balls 123, which, by then, are no longer in contact with the bottom wall 126 of the housing 121 and roll on the lateral race 129 under centrifugation forces, will then move along an orbit joining their centers so as to compensate for the decreasing unbalance of the rotor created by the whole blood in the first satellite bag 2 being transferred into the separation bag 1. The density of the balls in the housing 121 will first be higher in an area of the housing 121 opposite the first satellite bag 2 with respect to the rotation axis 31 of the rotor. Then, gradually, the balls 123 will move slightly away from the initial high density area until the first satellite bag 2 is empty and they are distributed around the rotor so as to compensate for the light unbalance caused by the weight of the filter 22 and the storage solution in the third satellite bag 4.

If the separation apparatus is fitted with a balancing apparatus 120 of the type shown in FIG. 14, which comprises stopping or parking elements, the balls 123, at the onset of the second stage, are engaged in the conic dents 132 around the housing 121 and are more or less evenly distributed around the rotor (at least they are not all stuck against each other, when the separation apparatus stands on uneven ground). As a result, the distance they will have to cover until they reach their balancing position after the speed of the rotor has exceeded the critical speed will be minimal, and the overall balancing effect will be reached faster than with the embodiment of the balancing assembly shown in FIGS. 11 to 13.

If the photo cell 56 has not detected red blood cell within a predetermined period of time following the start of the centrifugation process, the control unit 70 causes the rotor to stop and an alarm to be emitted. This could happen in particular if the frangible pin 16 has not been broken or if the clamp 15 on the first transfer tube 14 has not been opened.

Third stage (first protocol): the blood within the separation chamber is sedimented to a desired level.

At the onset of this stage, the pinch valve members 42, 43, 44 are closed. The rotor is rotated at a second, high centrifugation speed (for example, about 3200 RPM) for a predetermined period of time (for example, about 220 seconds) that is selected so that, whatever the hematocrit of the whole blood initially transferred in the separation bag 1, the blood sediments therein at the end of the predetermined period to a point where the hematocrit of the outer annular red blood cell layer is about 90 and the inner annular plasma layer is substantially devoid of cells. In more details, at the outcome of this sedimentation stage, the separations bag 1 exhibits four layers: a first inner layer mainly comprising plasma, a second intermediate layer mainly comprising platelets, a third intermediate layer mainly comprising mononuclear cells (lymphocytes and monocytes), and a fourth outer layer mainly comprising red blood cells (granulocytes remain embedded in the most inner layer of red blood cells).

Fourth stage (first protocol): a plasma component is transferred into the first satellite bag 2.

At the onset of this stage, the pinch valve members 42, 43, 44 are closed. The rotor is rotated at the same high centrifugation speed as in the sedimentation stage. After a predetermined period of time after the bag sensor 56 has stopped detecting red blood cells, which can happen before the end of the predetermined sedimentation period, the third pinch valve member 44 controlling the access to the second satellite bag 3 is opened and the pumping station 60 is actuated so as to pump hydraulic liquid at a constant flow rate (for example, about 220 ml/min) into the hydraulic chamber 55. The expanding hydraulic chamber 55 squeezes the separation bag 1 and causes the transfer of plasma into the second satellite bag 3. The pumping station 60 is stopped and the third pinch valve member 44 is closed after a predetermined period of time has elapsed following the detection of red blood cells by the bay sensor 57. A small volume of plasma (for example, about 5 ml) remains in the separation bag 1.

The transfer flow rate of the plasma component (which is directly related to the flow rate of the hydraulic fluid) is selected to be as high as possible without disturbing the platelet layer so as to avoid contaminating the plasma component with platelets.

During the fourth stage, the balls 123 of the balancing apparatus 120 (135) move along the orbit joining their centers so as to compensate for the increasing unbalance of the rotor created by the plasma component being transferred from the separation bag 1 into the second satellite bag 3. The density of the balls in the housing 121 will then be higher in an area of the housing 121 opposite the second satellite bag 3 with respect to the rotation axis 31 of the rotor.

Fifth stage (first protocol): a platelet/mononuclear cell component is transferred into the first satellite bag 2.

The fifth stage can start as soon as the third pinch valve member 44 is closed at the end of the fourth stage. At the onset of this fifth stage, the pinch valve members 42, 43, 44 are closed. The rotor is rotated at the same high centrifugation speed as previously. The first pinch valve member 42 controlling the access to the first satellite bag 2 is opened and the pumping station 60 is actuated so as to pump hydraulic liquid at a constant flow rate (for example, about 140 ml/min) into the hydraulic chamber 55. The expanding hydraulic chamber 55 squeezes the separation bag 1 and causes the transfer, into the first satellite bag 2, of a platelet/mononuclear cell component comprising the residual volume of plasma, the platelets, lymphocytes, monocytes and a small amount of red blood cells. The pumping station 60 is stopped and the first pinch valve member 42 is closed after a predetermined volume has been transferred into the first satellite bag 2, that is also after a predetermined amount of time has elapsed for a given hydraulic liquid flow rate. This predetermined volume of platelet/mononuclear cell component depends in part on the residual amount of plasma in the separation bag 1 at the end of the fourth stage. For example, when the residual volume of plasma in the separation bag 1 is determined by the bay sensor 57, the predetermined volume of the platelet/mononuclear cell component can be set at about between 10 and 15 ml, including about 5 ml of plasma and about 5 ml of red bloods cells.

During the fifth stage, the balls 123 of the balancing apparatus 120 (135) slightly move along the orbit joining their centers so as to compensate for the increasing, light unbalance of the rotor created by platelet/mononuclear cell component being transferred from the separation bag 1 into the first satellite bag 2. The density of the balls in the housing 121 will then slightly increase in an area of the housing 121 opposite the first satellite bag 2 with respect to the rotation axis 31 of the rotor.

Sixth stage (first protocol): the storage solution for red blood cells contained in the third satellite bag 3 is transferred into the separation bag 1.

The sixth stage can start as soon as the third pinch valve member 42 is closed at the end of the fifth stage. At the onset of this fifth stage, the pinch valve members 42, 43, 44 are closed. The rotor is rotated at the same high centrifugation speed as previously. The second pinch valve member 43 controlling the access to the third satellite bag 4 is opened, allowing the storage solution contained in the third satellite bag 3 to flow, under centrifugation forces, from the third satellite bag 3 into the separation bag 1, through the filter 22. After a predetermined period of time has lapsed after the opening of the second pinch valve member 43, the rotor is sharply braked so that its rotation speed decreases rapidly to a third, reduced speed (for example, 1500 RPM), so as to cause a suspension of the red blood cells contained in the separation bag in the storage solution and lower the viscosity thereof.

During the sixth stage, the balls 123 of the balancing apparatus 120 (135) slightly move along the orbit joining their centers so as to compensate for the decreasing, light unbalance of the rotor created by the red blood cell storage solution being transferred from the third satellite bag 4 into the separation bag 1. The density of the balls in the housing 121 will then slightly decrease in an area of the housing 121 opposite the third satellite bag 4 with respect to the rotation axis 31 of the rotor.

Seventh stage (first protocol): a red blood cell component is transferred into the third satellite bag 4.

The seventh stage can start after a predetermined period of time has lapsed after the rotor rotates at the third rotation speed. At the onset of this stage the second pinch valve member 43 controlling the access to the third satellite bag 4 is open and the pinch valve members 42, 44 are closed. The rotor rotates at the third rotation speed. The pumping station 60 is actuated so as to pump hydraulic liquid at a first flow rate into the hydraulic chamber 55 and consequently squeeze the separation bag 1 so as to cause the transfer, through the filter 22, of a red blood cell component into the third satellite bag 4. The first transfer flow rate of the red blood cell component (which is directly related to the flow rate of the hydraulic fluid) is selected to be as high as possible without damaging the red blood cells (hemolysis). When the pressure of the hydraulic liquid measured by the pressure gauge 67 reaches a first high pressure threshold, the flow rate of the hydraulic liquid is decreased from the first flow rate to a second flow rate. When the pressure of the hydraulic liquid measured by the pressure gauge 67 reaches a second high pressure threshold, the flow rate of the hydraulic liquid is further decreased from the second flow rate to a third flow rate. The second and third transfer flow rates of the red blood cell component are selected so that a maximal portion of the red blood cell component is transferred into the third satellite bag 4. The white blood cells (granulocytes and residual monocytes and lymphocytes) are trapped by the filter 22, so that the ultimate packed red blood cell component in the third satellite bag 4 is substantially devoid of white blood cells.

During the seventh stage, the balls 123 of the balancing apparatus 120 (140) move along the orbit joining their centers so as to compensate for the increasing unbalance of the rotor created by red blood cell component being transferred from the separation bag 1 into the third satellite bag 4. The density of the balls in the housing 121 will then increase in an area of the housing 121 opposite the third satellite bag 4 with respect to the rotation axis 31 of the rotor.

Eighth stage (first protocol): the centrifugation process is ended. When a predetermined period of time (for example, about 30 seconds) has lapsed after the pressure of the hydraulic liquid has reached the second pressure threshold, the rotation speed of the rotor is decreased until the rotor stops, the pumping station 60 is actuated so as to pump the hydraulic liquid from the hydraulic chamber 55 at a high flow rate (for example, about 800 ml/min) until it the hydraulic chamber 55 is empty, and the three pinch valve members 42, 43, 44 are actuated so as to seal and cut the tubes 14, 20, 21.

Variants of the first protocol are as follows: the volume of anti-coagulated whole blood contained in the first satellite bag 2 is transferred by gravity into the separation bag 1 before the separation process is started. The initial unbalance of the rotor is therefore limited to the weights of the filter 22 and of the storage solution for red blood cells contained in the third satellite bag 4. The separation apparatus is stopped after the platelet/mononuclear cell component has been transferred into the first satellite bag 2. The transfer of the storage solution from the third satellite bag 4 into the separation bag 1 and the transfer of the red blood cell component from the separation bag 1 into the third satellite bag 4 will be done later, by gravity. The final unbalance of the rotor therefore amounts to the weight of the filter 22, of the storage solution for red blood cells contained in the third satellite bag 4, of the plasma component contained in the second satellite bag 3, and of the platelet/mononuclear cell component contained in the first satellite bag 2. The bag set used does not comprise a third satellite bag and a leuko-reduction filter. When the plasma component has been transferred into the second satellite bag 3, all the blood cells (platelets, white cells and red blood cells), which remain in the separation bag 1, are transferred into the first satellite bag 2.

An example of a second separation protocol aiming at washing a volume of thawed glycerolized red blood cells, is explained bellow. This second separation protocol does not require the use of the second pinch valve member 43 nor of the channel sensor 58. The operation of the separation apparatus along the second separation protocol is as follows:

First stage (second protocol): a bag set as shown in FIG. 2, in which a satellite bag contains a volume of thawed glycerolized red blood cells, is set in place in the rotor of a centrifuge (as shown in FIGS. 3, 4).

At the onset of the first stage, a first satellite bag 2 containing a volume of thawed glycerolized red blood cells has been connected to the separation bag 1 by the first transfer tube 14. The second satellite bag 3, which contains a volume of wash liquid, and the first satellite bag 2 are engaged on the first couple of pegs 107, 108 of a bag holder 100, the second satellite bag 3 being engaged first. The third satellite bag 4 is engaged on the second couple of pegs 111, 112. The bag holder 100 is mounted in a cradle 87 (as shown in FIGS. 7, 8, 9), as a result of which the first satellite bag 2 is adjacent to the inner surface of the cradle 87. The cradle 87 is inserted into the central compartment 34 of a centrifuge (as shown in FIGS. 3 and 4) so as to fit with the remaining part of the bag vessel 79. The collection bag 1 is laid on the turntable 35 and the pins 83 on the flange 82 of the bag vessel 79 are engaged in the holes 12 of the disk-shaped connecting element 9 of the separation bag 1. The first transfer tube 14 connecting the first satellite bag 2 to the separation bag 1 is engaged in the first pinch valve member 42 and second transfer tube 20 connecting the second satellite bag 3 to the separation bag 1 is engaged in the third pinch valve member 44. The clamps 15 on the first and second transfer tubes 14, 20 are open. The frangible pin 16 blocking communication between the first satellite bag 2 and the separation bag 1 is broken, as well as the frangible pin 25 blocking communication between the second satellite bag 3 and the separation bag 1, so that communication is established between the two satellite bags 2, 3 and the separation bag 1. The lid 49 of the rotor is closed.

Second stage (second protocol): the volume of thawed glycerolized red blood cells contained in the first satellite bag 2 is transferred into the separation bag 1.

This stage is substantially the same as the second stage of the first protocol. At the end of this stage, the second satellite bag 3 containing the wash solution is stuck onto the inner surface of the cradle 87 by the centrifugal forces.

Third stage (second protocol): the thawed glycerolized red blood cells are sedimented to a desired level.

This stage is substantially the same as the third stage of the first protocol. At the outcome of this sedimentation stage, the separation bag 1 exhibits two layers: a first inner layer mainly comprising a supernatant (essentially glycerol) and a second outer layer comprising red blood cells.

Fourth stage (second protocol): the glycerol is transferred into the first satellite bag 2.

This stage is substantially the same as the fourth stage of the first protocol, except that the supernatant or glycerol is transferred into the first satellite bag 2, which initially contained the volume of thawed glycerolized red blood cells.

Fifth stage (second protocol): a first volume of wash liquid is transferred from the second satellite bag 3 into the separation bag 1.

At the onset of this stage, the first and third pinch valve members 42, 44 are closed. The centrifuge rotates at the same high centrifugation speed as during the sedimentation stage. The third pinch valve member 44 is opened for a predetermined amount of time so as to allow the transfer, under centrifugation forces, of a first volume of wash liquid into the separation bag 1. For example, the third pinch valve 44 member is opened for as long as it takes to transfer half of the volume of the wash liquid. Alternately, the third pinch valve member 44 is opened until the bag sensor 56 detects a liquid in the separation bag 1.

Sixth stage (second protocol): the red blood cells are suspended in the first volume of wash liquid.

At the onset of this stage, the first and third pinch valve members 42, 44 are closed. The rotor is sharply braked so that its rotation speed decreases rapidly to a second, reduced speed so as to cause a suspension of the red blood cells contained in the separation bag in the wash liquid.

The next stages of the second protocol substantially repeat stages 3, 4, 5, 6, and then repeat stages 3 and 4. That is, the red blood cells suspended in the first volume of wash liquid are separated by centrifugation, the supernatant (wash liquid and glycerol) is transferred into the first satellite bag 2 by the hydraulic station 60, a second volume of wash liquid (e.g. the second remaining half of the initial volume) is transferred under centrifugal forces into the separation bag 1, the red blood cells are suspended in the second volume of wash liquid and separated again by centrifugation, and the supernatant is transferred into the first satellite bag 2 by the hydraulic station 60. What remains then in the separation bags 1 are the washed red blood cells.

Seventh stage (second protocol): the centrifugation process is ended.

The rotation speed of the rotor is decreased until the rotor stops, the pumping station 60 is actuated so as to pump the hydraulic liquid from the hydraulic chamber 55 at a high flow rate (for example, about 800 ml/min) until the hydraulic chamber 55 is empty, and the first and third pinch valve members 42, 44 are actuated so as to seal and cut the first and second transfer tubes 14 and 20. The washed red blood cells remain in the separation bag 1.

Eighth stage (second protocol): the washed blood cells are transferred into the third satellite bag 4.

The lid 49 of the rotor is opened and the separation bag 1 connected to the third satellite bag 4 is removed from the rotor. The clamp 15 on the third transfer tube 21 is opened. The frangible pin 23 blocking the communication between the third satellite bag 4 and the third transfer tube 21 connected thereto is broken. The content of the separation bag 1 is then allowed to flow by gravity into the third satellite bag 4. The third transfer tube 21 is sealed and cut.

The operation of the balancing apparatus 120 (135) during the implementation of the second protocol does not substantially differ from its operation during the implementation of the first protocol. The unbalance of the rotor is however substantial during the whole separation process, and its fluctuates following the red blood cell washing cycles.

In the third stage, when the rotor starts rotating, the balls 123 move in an inordinate manner in the housing 121 until the speed of the rotor exceeds a critical speed that coincides with the resonance frequency of the rigid body modes of the rotor. The balls 123 move then along an orbit joining their centers so as to compensate for the unbalance of the rotor created by the wash liquid in the second satellite bag 3. The density of the balls 123 in the housing 121 become higher in an area of the housing 121 opposite the second satellite bag 3 with respect to the rotation axis 31 of the rotor.

During the fourth stage (and its subsequent repetitions), the balls 123 move along the orbit joining their centers so as to compensate for the increasing unbalance of the rotor created by the glycerol/used wash liquid being transferred from the separation bag 1 into the first satellite bag 2. The density of the balls in the housing 121 become higher in an area of the housing 121 opposite the first satellite bag 2 with respect to the rotation axis 31 of the rotor.

During the fifth stage (and its subsequent repetition), the balls 123 move along the orbit joining their centers so as to compensate for the decreasing unbalance of the rotor created by a volume of wash liquid being transferred from the second satellite bag 3 into the separation bag 1. The density of the balls in the housing 121 decreases in an area of the housing 121 opposite the first and second satellite bag 2, 3 with respect to the rotation axis 31 of the rotor.

Figure 15:
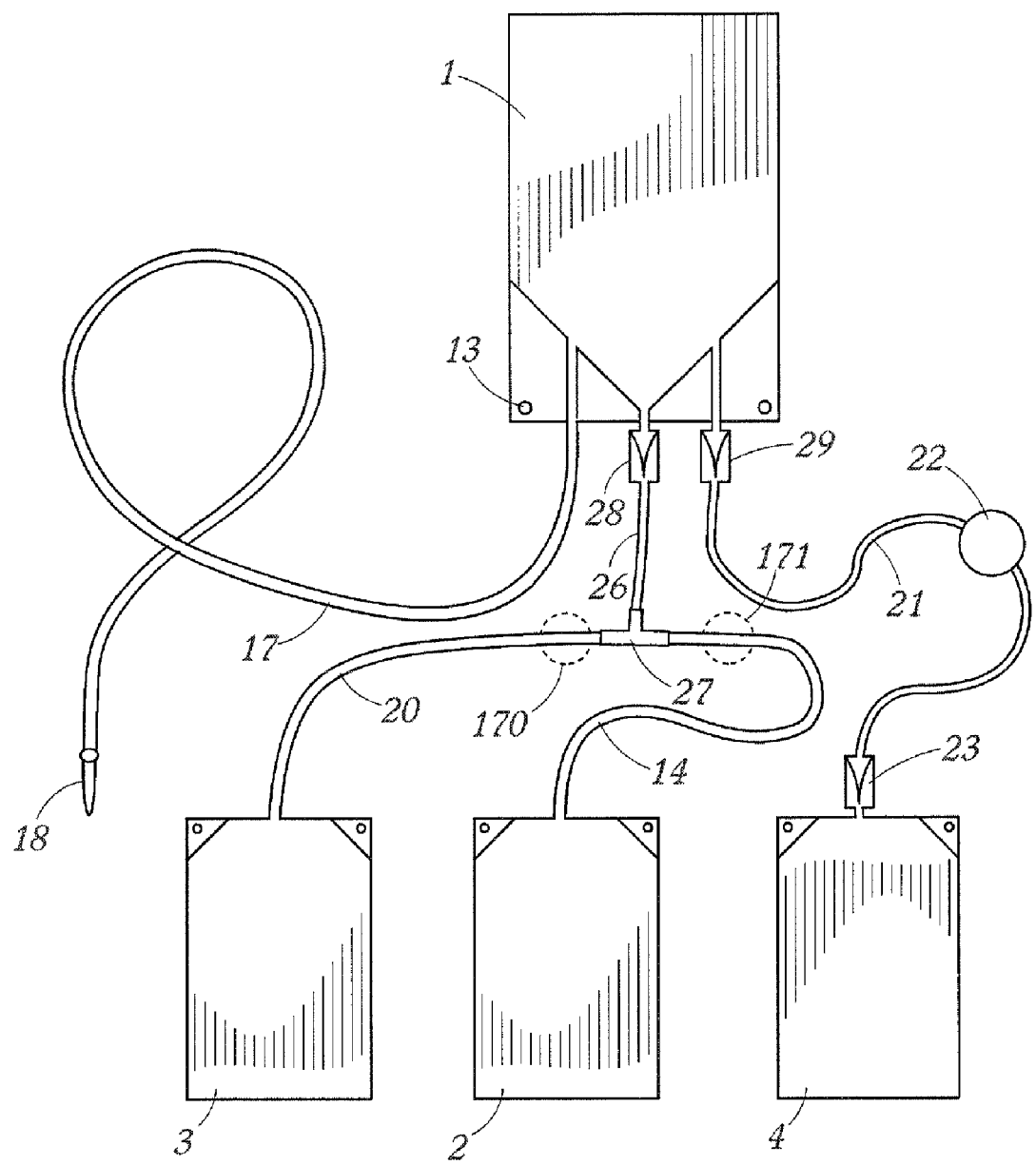
FIG. 15 is a schematic view of third set of separation and collection bags for cooperating with a separation apparatus.

FIG. 15 shows an example of a set of bags that is designed for cooperating with a separation apparatus that can simultaneously separate a plurality of discrete volumes of a composite liquid into at least two components. The set of bags of FIG. 15 is adapted to the separation of a composite liquid (e.g. whole blood) into a first component (e.g. a plasma component), an intermediate component (e.g. a platelet component), and a second component (e.g. a red blood cell component). This bag set comprises a flexible separation bag 1 and three flexible satellite bags 2, 3, 4 connected thereto.

When the composite liquid is whole blood, the separation bag 1 has two purposes, and is successively used as a collection bag and as a separation bag. It is intended for initially receiving a discrete volume of whole blood from a donor (usually about 450 ml) and to be used later as a separation chamber in a separation apparatus. The separation bag 1 is flat and generally rectangular. It is made of two rectangular sheets of plastic material that are welded together so as to define therebetween an interior space having a main rectangular portion connected to a triangular top downstream portion. A first tube 26 is connected to the tip of the triangular portion, and a second and a third tubes 17, 21 are connected to either lateral edges of the triangular portion, respectively. The proximal ends of the three tubes 17, 21, 26 are embedded between the two sheets of plastic material so as to be parallel. The separation bag 1 further comprises a hole 13 in each of its corners that are adjacent to the three tubes 17, 21, 26. The holes 13 are used to secure the separation bag 1 to a separation cell, as will be described later.

The separation bag 1 initially contains a volume of anticoagulant solution (typically about 63 ml of a solution of citrate phosphate dextrose for a blood donation of about 450 ml), and the first and third tubes 26, 21 are fitted at their proximal end with a breakable stopper 28, 29 respectively, blocking a liquid flow therethrough.

The first satellite bag 3 is intended for receiving a plasma component and the second satellite bag 2 is intended for receiving a platelet component. The first and the second satellite bags 2, 3 are flat and substantially rectangular. They are connected, by a fourth and a fifth tubes 20, 14 respectively, to the two arms of a T-shaped three-way connector 27, having its leg connected to the distal end of the first tube 26.

The third satellite bag 4 is intended for receiving a red blood cell component. It is flat and substantially rectangular. It is connected to the distal end of the third tube 21. The third tube 21 comprises two segments respectively connected to the inlet and the outlet of a leuko-reduction filter 22. The second satellite bag 4 contains a volume of storage solution for red blood cells, and the third tube 21 is fitted at its distal end with a breakable stopper 23 blocking a liquid flow therethrough.

The second tube 17 is a collection tube having a needle 18 connected to its distal end. At the beginning of a blood donation, the needle 18 is inserted in the vein of a donor and blood flows into the collection (separation) bag 1. After a desired volume of blood has been collected in the collection (separation) bag 1, the collection tube 17 is sealed and cut.

Figure 16:
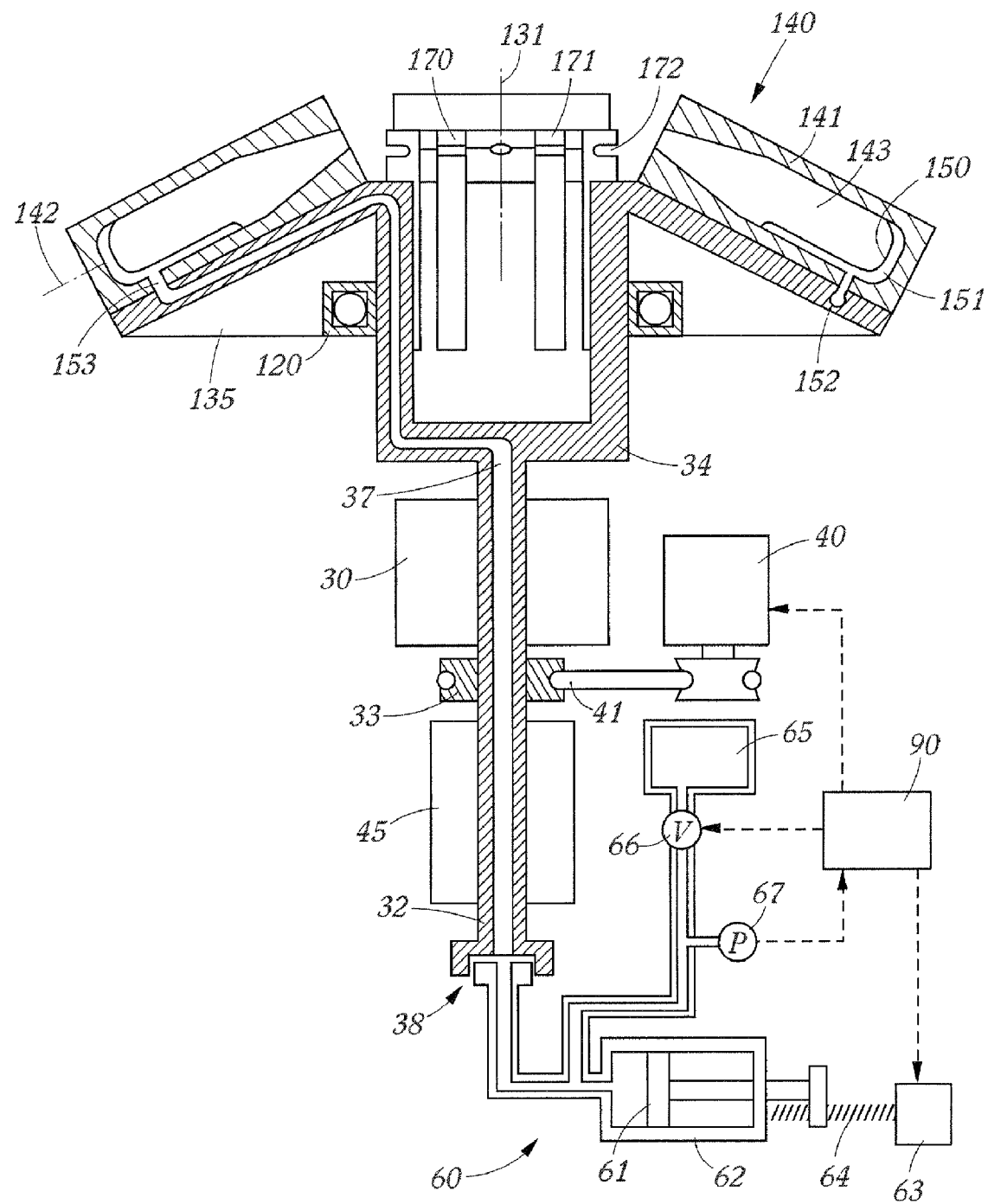
FIG. 16 is a schematic view, partly in cross-section along a diametral plane, of a third embodiment of a separation apparatus.
Figure 17:
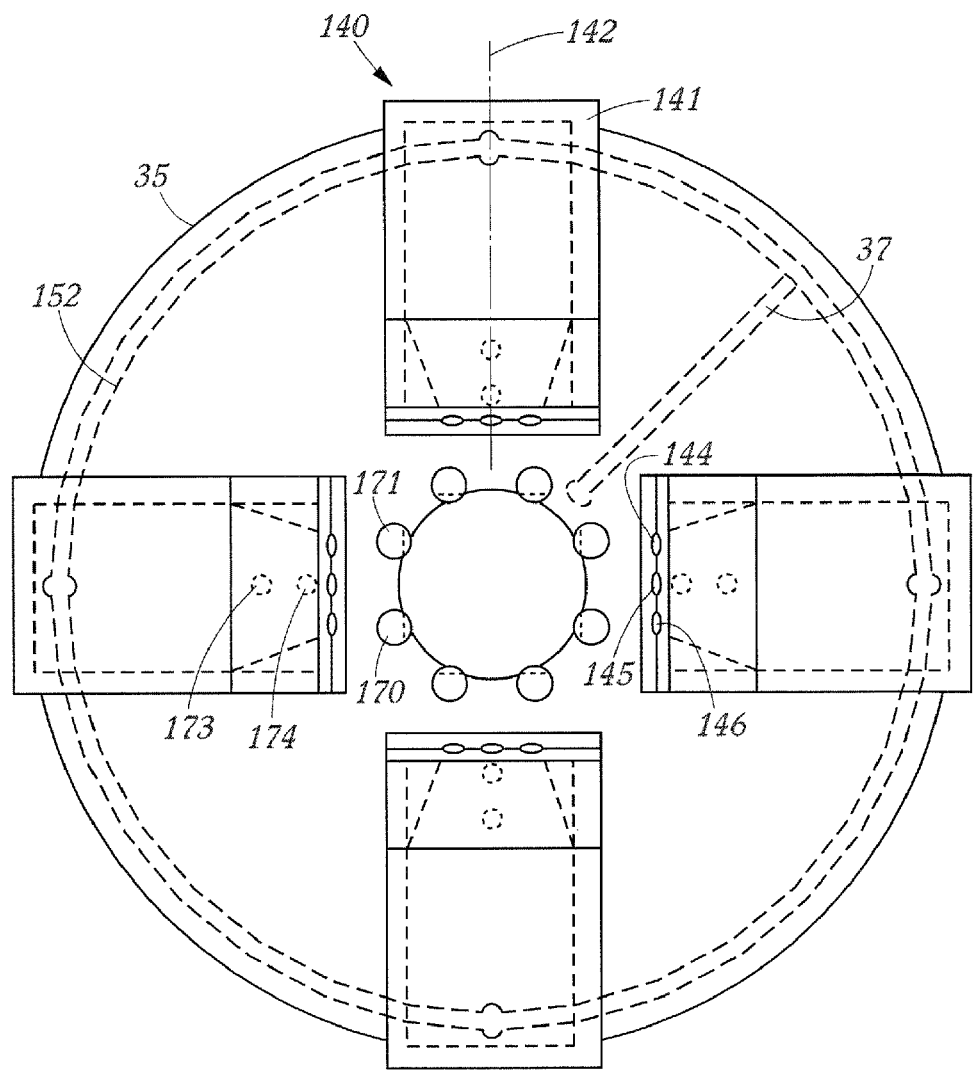
FIG. 17 is a top view of the rotor of the separation apparatus of FIG. 16.
Figure 18:
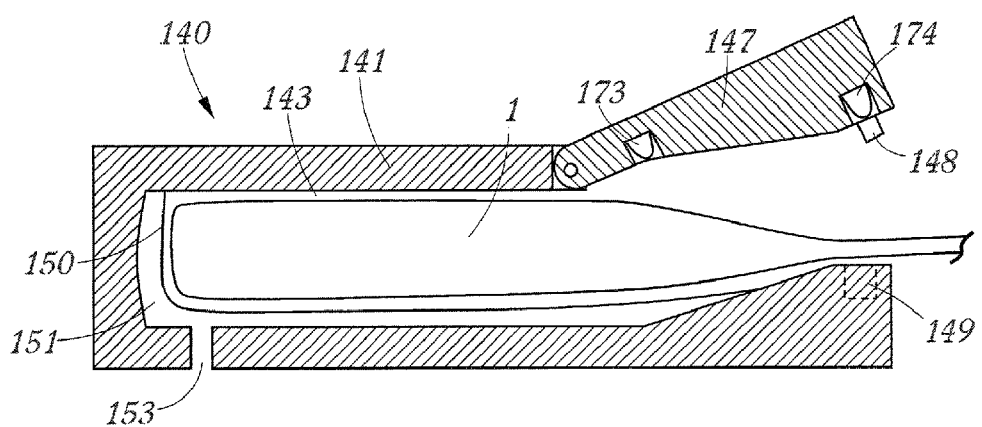
FIG. 18 is schematic view, in cross-section along a radial plane, of a separation cell of the separation apparatus of FIGS. 16 and 17.

FIGS. 16, 17, 18 show a third embodiment of a separation apparatus. This separation apparatus is designed for simultaneously separating by centrifugation four discrete volumes of a composite liquid (e.g. whole blood).

The third separation apparatus comprises: a centrifuge adapted to receive four set of bags shown in FIG. 15, with the four discrete volumes of a composite liquid contained in the four separation bags; a component transferring system for transferring at least one separated component from each separation bag into a satellite bag connected thereto; a balancing apparatus for initially balancing the rotor when the weights of the four separation bags are different and for balancing the rotor when the weights of the separated components later transferred into the satellite bags cause an unbalance of the rotor.

The centrifuge of this third separation apparatus is similar to the centrifuge of the first and second separation apparatuses shown in FIGS. 3 and 4, to the extent that it comprises a rotor that is supported by a bearing assembly 30 allowing the rotor to rotate around a rotation axis 31. The rotor comprises a cylindrical rotor shaft 32 to which a pulley 36 is connected; a storage element comprising a central cylindrical container 34 for containing satellite bags, which is connected to the rotor shaft 32 at the upper end thereof so that the longitudinal axis of the rotor shaft 32 and the longitudinal axis of the container 34 coincide with the rotation axis 31; and a frusto-conical turntable 35 connected to the upper part of the central container 34 so that its central axis coincides with the rotation axis 31. The frusto-conical turntable 35 flares underneath the opening of the container 34; a balancing assembly 120, which is secured to the turntable 35; and the centrifuge further comprises a motor 40 coupled to the rotor by a belt 41 engaged in a groove of the pulley 36 so as to rotate the rotor about the rotation axis 31.

The centrifuge of the third separation apparatus differs from the centrifuge of the first and second separation apparatuses shown in FIGS. 3 and 4 essentially in as much as it is adapted for receiving four separation bags 1 at the same time. For this purpose, it comprises four identical separation cells 140 are mounted on the turntable 35 so as to form a symmetrical arrangement with respect to the rotation axis 31.

Each separation cell 140 comprises a container 141 having the general shape of a rectangular parallelepiped. The separation cells 140 are mounted on the turntable 35 so that their respective median longitudinal axes 142 intersect the rotation axis 31, so that they are located substantially at the same distance from the rotation axis 31, and so that the angles between their median longitudinal axes 142 are substantially the same (i.e. 90 degrees). The exact position of the separation cells 140 on the turntable 35 is adjusted so that the weight on the turntable is equally distributed when the separation cells 140 are empty, i.e. so that the rotor is balanced. It results from the arrangement of the separating cells 140 on the turntable 35 that the separating cells 140 are inclined with respect to the rotation axis 31 of an acute angle equal to the angle of the frustum of a cone that geometrically defines the turntable 35.

Each container 141 comprises a cavity 143 that is so shaped and dimensioned as to loosely accommodate a separation bag 1 full of liquid, of the type shown in FIG. 15. The cavity 143 (which will be referred to later also as the "separation compartment") is defined by a bottom wall, that is the farthest to the rotation axis 31, a lower wall that is the closest to the turntable 35, an upper wall opposite to the lower wall, and two lateral walls. The cavity 143 comprises a main part, extending from the bottom wall, which has substantially the shape of a rectangular parallelepiped with rounded angles, and an upper part, which has substantially the shape of a prism having convergent triangular bases. In other words, the upper part of the cavity 143 is defined by two couples of opposite walls converging towards the central median axis 142 of the cavity 143. One interest of this design is to cause a radial dilatation of the thin layer of a minor component of a composite fluid (e.g. the platelets in whole blood) after separation by centrifugation, and makes it more easily detectable in the upper part of a separation bag. The two couples of opposite walls of the upper part of the separation cell 140 converge towards three cylindrical parallel channels 144, 145, 146 (FIG. 17), opening at the top of the container 141, and in which, when a separation bag 1 is set in the container 141, the three tubes 17, 21, 26 extend.

The container 141 also comprises a hinged lateral lid 147, which is comprised of an upper portion of the external wall of the container 141, i.e. the wall that is opposite to the turntable 35. The lid 147 is so dimensioned as to allow, when open, an easy loading of a separation bag 1 full of liquid into the separation cell 140. The container 141 comprises a fast lock (not shown) by which the lid 147 can be locked to the remaining part of the container 141.

The container 141 also comprises a securing apparatus for securing a separation bag 1 within the separation cell 140. The bag securing apparatus comprises two pins 148 protruding on the internal surface of the lid 147, close to the top of separation cell 140, and two corresponding recesses 149 in the upper part of the container 141. The two pins 148 are so spaced apart and dimensioned as to fit into the two holes 13 in the upper corner of a separation bag 1.

The separation apparatus further comprises a component transferring system for transferring at least one separated component from each separation bag into a satellite bag connected thereto. The component transferring system comprises a squeezing system for squeezing the separation bags 1 within the separation compartments 143 and causing the transfer of separated components into satellite bags 2, 3, 4.

The squeezing system comprises a flexible diaphragm 150 that is secured to each container 141 so as to define an expandable chamber 151 in the cavity thereof. More specifically, the diaphragm 150 is dimensioned so as to line the bottom wall of the cavity 143 and a large portion of the lower wall of the cavity 143, which is the closest to the turntable 35.

The squeezing system further comprises a peripheral circular manifold 152 that forms a ring within the turntable 35 extending close to the periphery of the turntable 35. Each expansion chamber 151 is connected to the manifold 152 by a supply channel 153 that extends through the wall of the respective container 141, close to the bottom thereof.

The squeezing system further comprises a hydraulic pumping station 60 for pumping a hydraulic liquid in and out the expandable chambers 151 within the separation cells 140. The pumping station 60 is similar to the pumping station of the separation apparatus shown in FIG. 3.

The third embodiment of separation apparatus further comprises four pairs of a first and second pinch valve members 170, 171 that are mounted on the rotor around the opening of the central container 34. Each pair of pinch valve members 170, 171 faces one separation cell 140, with which it is associated. The pinch valve members 170, 171 are designed for selectively blocking or allowing a flow of liquid through a flexible plastic tube, and selectively sealing and cutting a plastic tube. Each pinch valve members 170, 171 comprises an elongated cylindrical body and a head having a groove 172 that is defined by a stationary upper jaw and a lower jaw movable between an open and a closed position. The groove 172 is so dimensioned that one of the tubes 14, 20 of the bag sets shown in FIGS. 1 and 2 can be snuggly engaged therein when the lower jaw is in the open position. The elongated body contains a mechanism for moving the lower jaw and it is connected to a radio frequency generator that supplies the energy necessary for sealing and cutting a plastic tube. The pinch valve members 170, 171 are mounted inside the central container 34, adjacent the interior surface thereof, so that their longitudinal axes are parallel to the rotation axis 31 and their heads protrude above the rim of the container 34. The position of a pair of pinch valve members 170, 171 with respect to a separation bag 1 and the tubes 14, 20 connected thereto when the separation bag 1 rests in the separation cell 140 associated with this pair of pinch valve members 170, 171 is shown in doted lines in FIG. 15. Electric power is supplied to the pinch valve members 170, 171 through a slip ring array 45 that is mounted around a lower portion of the rotor shaft 32.

The separation apparatus further comprises four pairs of sensors 173, 174 for monitoring the separation of the various components occurring within each separation bag when the apparatus operates. Each pair of sensors 173, 174 is embedded in the lid 147 of the container 141 of each separation cell 140 along the median longitudinal axis 142 of the container 141, a first sensor 173 being located the farthest and a second sensor 174 being located the closest to the rotation axis 31. When a separation bag 1 rests in the container 141 and the lid 147 is closed, the first sensor 173 (later the bag sensor) faces the upper triangular part of the separation bag 1 and the second sensor 174 (later the tube sensor) faces the proximal end of the first tube 26. The bag sensor 173 is able to detect blood cells in a liquid. The tube sensor 174 is able to detect the presence or absence of liquid in the tube 4 as well as to detect blood cells in a liquid. Each sensor 173, 174 may comprise a photocell including an infrared LED and a photo-detector. Electric power is supplied to the sensors 173, 174 through the slip ring array 45 that is mounted around the lower portion of the rotor shaft 32.

As mentioned above, the third separation apparatus comprises a balancing system for initially balancing the rotor when the weights of the four separation bags 1 contained in the separation cells 140 are different, which is typically the case. The balancing system also balances the rotor when the separated components are later transferred from the separations bags 1 into corresponding satellite bags 2, 3, 4. The unbalance of the rotor can then result from two causes: first, the centrifuge can be controlled so as to transfer successively (as opposed to simultaneously) the same separated component (e.g. a platelet component) from each separation bag 1 into the corresponding component bags 2, 3 or 4 connected thereto; second, the four volumes of the same component transferred into the satellite bags 2, 3 or 4 in the central container 34 can be different. For example, when two blood donations have the same hematocrit and different volumes, the volumes of plasma extracted from each donation are different, and the same is true when two blood donations have the same volume and different hematocrit.

The balancing system comprise a balancing assembly 120, which is similar to one of the balancing assemblies shown in FIGS. 11 to 14 and described above. The balancing assembly 120 is mounted on the rotor within the space that extends between the upper end of the central container 34 and the frusto-conical wall 46 of the turntable 35. It results from this arrangement that the upper balancing assembly is located underneath the turntable 35.

The separation apparatus further comprises a controller 70 including a control unit (e.g. a microprocessor) and a memory unit for providing the microprocessor with information and programmed instructions relative to various separation protocols (e.g. a protocol for the separation of a plasma component and a blood cell component, or a protocol for the separation of a plasma component, a platelet component, and a red blood cell component) and to the operation of the apparatus in accordance with such separation protocols. In particular, the microprocessor is programmed for receiving information relative to the centrifugation speed(s) at which the rotor is to be rotated during the various stages of a separation process (e.g. stage of component separation, stage of a plasma component expression, stage of suspension of platelets in a plasma fraction, stage of a platelet component expression, etc), and information relative to the various transfer flow rates at which separated components are to be transferred from the separation bags 1 into the satellite bags 2, 3, 4. The information relative to the various transfer flow rates can be expressed, for example, as hydraulic liquid flow rates in the hydraulic circuit, or as rotation speeds of the stepper motor 63 of the hydraulic pumping station 60. The microprocessor is further programmed for receiving, directly or through the memory, information from the pressure gauge 67 and from the four pairs of photocells 173, 174 and for controlling the centrifuge motor 40, the stepper motor 63 of the pumping station 60, and the four pairs of pinch valve members 170, 171 so as to cause the separation apparatus to operate along a selected separation protocol.

Figure 19:
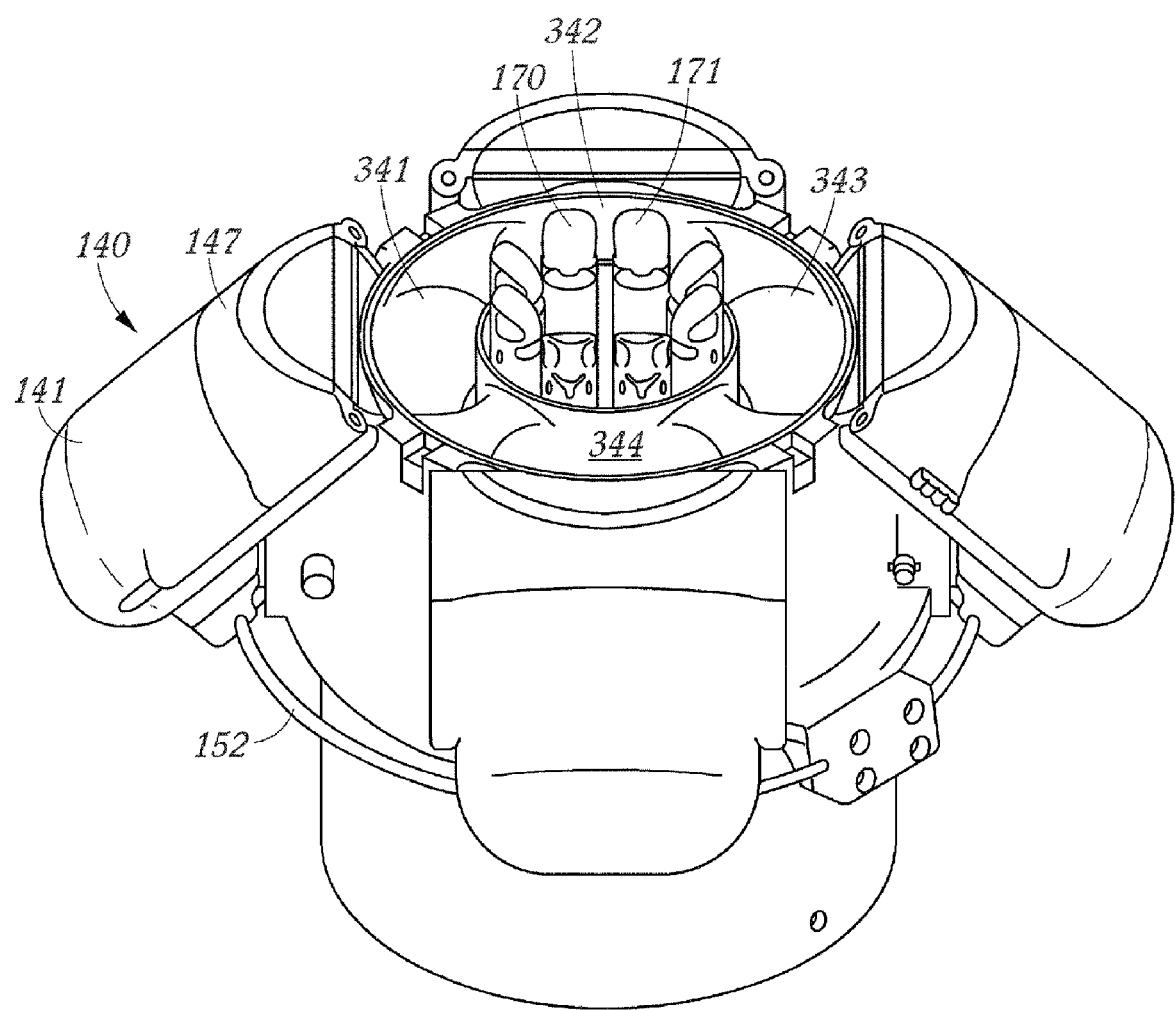
FIG. 19 is a perspective view of a rotor of a fourth embodiment of a separation apparatus.
Figure 20:
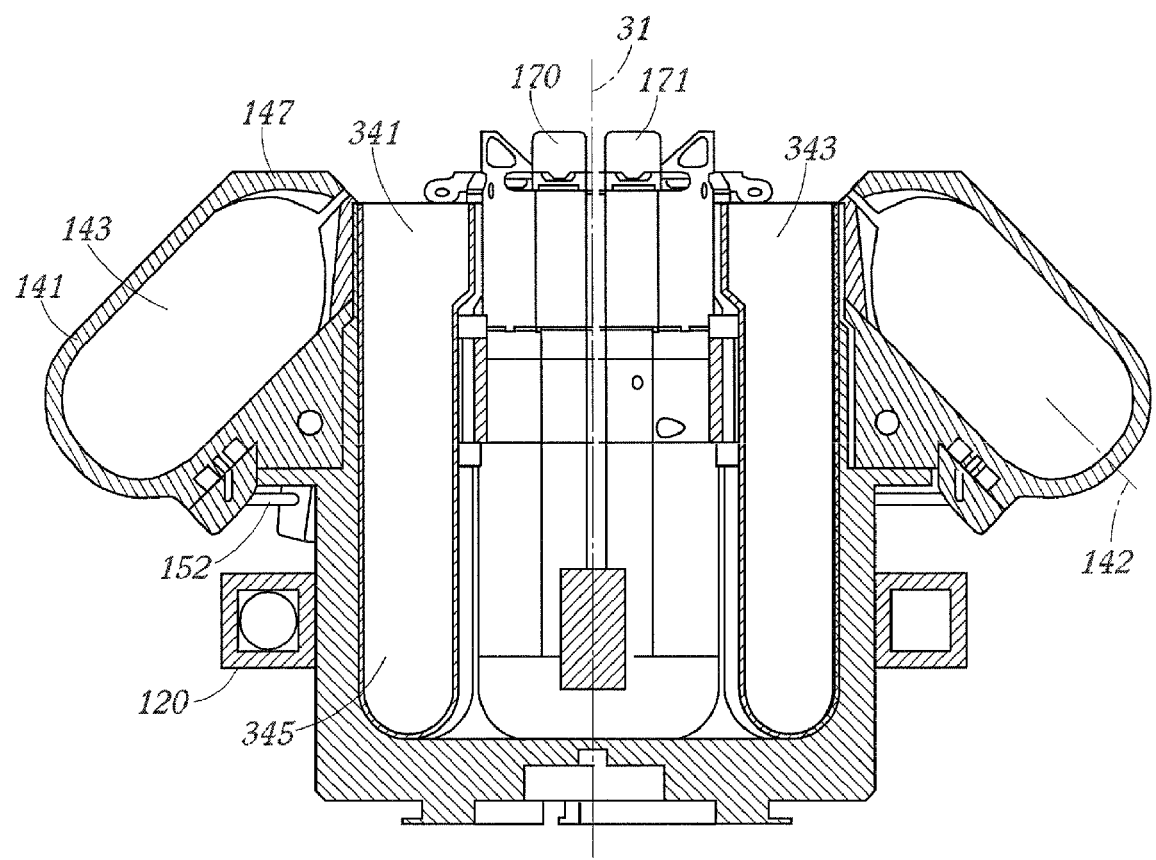
FIG. 20 is a cross-section view of the rotor of FIG. 19, along a diametral plane.

FIGS. 19, 20 show the rotor of a fourth embodiment of a separation apparatus for four discrete volumes of a composite liquid.

The rotor of this second embodiment essentially differs from the rotor of the embodiment of FIGS. 16 to 18 in the spatial arrangement of the pinch valve members 170, 171 and of the storage element for the satellite bags with respect to the separation cells 140. In this embodiment, the storage element, instead of comprising a central container, comprises four satellite containers 341, 342, 343, 344 that are arranged around a central cylindrical cavity 340, in which the four pairs of pinch valve member 170, 171 are mounted with their longitudinal axes parallel to the rotation axis 31. The cavity 345 of a satellite container 341, 342, 343, 344 has a regular bean-like cross-section, and a central longitudinal axis that is parallel to the rotation axis 31 and intersects the longitudinal axis 142 of the associated separation cell 140.

The rotor shown in FIGS. 19 and 20 is also fitted with a balancing assembly 120, which is secured to the cylindrical bucket containing the four satellite containers 341, 342, 343, 344, underneath the level of the separation cells 140. As in the embodiment of separation apparatus of FIGS. 16 to 14, the balancing assembly 120 initially plays a role when the rotor stars rotating while being unbalanced because the four separation bags 1 in the four separation cells 140 have different weights. The balls within the housing of the balancer 140 will then move so as to occupy positions around the cylindrical bucket by which they neutralize the unbalance of the rotor. The balancing assembly 120 will be solicited again later, whenever a separated component is transferred from the four separation bags into corresponding satellite bags 2, 3, 4 in the satellite containers 341, 342, 343, 344, and the final volume of the transferred component varies from one satellite bag to another.

Although the above apparatus has been described with respect to specific protocols it is understood that the apparatus and the balancing assembly can be used with additional protocols.

It will be apparent to those skilled in the art that various modifications can be made to the apparatus and method described herein. Thus, it should be understood that the invention is not limited to the subject matter discussed in the specification. Rather, the present invention is intended to cover modifications and variations.

The invention claimed is:

1. An apparatus for separating at least one volume of a composite liquid into at least a first component and a second component, the apparatus comprising:
   a centrifuging means having a rotation axis, comprising:
      a first containing means for storing a liquid at a distance from the rotation axis, whereby the storage of a liquid in the first containing means can cause an unbalance of the centrifuging means;
      a second containing means for storing a liquid at a distance from the rotation axis, whereby the storage of a liquid in the second containing means can cause an unbalance of the centrifuging means;
   a liquid transferring means for transferring a liquid between at least one of the first containing means and the second containing means whereby the transfer of a liquid can cause an unbalance of the centrifuging means;
      wherein the transferring means transfers a liquid from at least one satellite bag contained in the second containing means into at least one separation bag contained in the first containing means;
      wherein the transferring means comprises a support means for supporting at least one satellite bag within the second containing means so that the supported satellite bag has a lower portion that is closer to the axis of rotation than an upper portion thereof by which the supported satellite bag is connected to the separation bag, and so that a liquid contained in the supported satellite bag drains from the supported satellite bag into the separation bag under centrifugation forces when the rotor is rotated at a transfer rotation speed;
      wherein the support means comprises:
         a wall that is inclined with respect to the rotation axis;
         a securing means for securing an upper portion of the supported satellite bag to an upper part of the inclined wall so that the supported satellite bag containing a liquid that is secured to the inclined wall by the securing means is adjacent to the inclined wall; and a balancing means for substantially neutralizing an unbalance of the centrifuging means as it occurs.

2. An apparatus according to claim 1, wherein the balancing means comprises at least one balancing assembly comprising:
a plurality of ponderous satellites; and
a housing for containing the ponderous satellites and defining a circular orbit along which the ponderous satellites can move substantially freely.

3. An apparatus according to claim 2, wherein the at least one balancing assembly further comprises a plurality of stopping means for temporarily stopping the ponderous satellites when the centrifuging means does not rotate and the balancing assembly is inclined to no more than a predetermined angle with respect to a horizontal plane, and for allowing a movement of the ponderous satellites in the housing when the centrifuging means is rotating at a speed that is above a determined speed.

4. An apparatus according to claim 3, wherein the housing comprises a bottom wall, the plurality of ponderous satellites comprises a plurality of balls, and the stopping means comprises a plurality of dents in the bottom wall that are so shaped that a ball can partially engage in a dent.

5. An apparatus according to claim 4, wherein the dents of the stopping means have a substantially conic shape.

6. An apparatus according to claim 3, wherein the housing comprises a bottom wall, the plurality of ponderous satellites comprises a plurality of balls, and the stopping means comprises a plurality of protruding elements on the bottom wall.

7. An apparatus according to claim 3, wherein the stopping means are so shaped that a ponderous satellite stopped by a stopping means gets released therefrom when the balancing assembly is inclined with respect to a horizontal plane of more than between about 15 degrees and about 20 degrees.

8. An apparatus according to claim 3, wherein the number of stopping means is between about the number of ponderous satellites and about twice the number of ponderous satellites.

9. An apparatus according to claim 2, wherein the number of ponderous satellites is selected so that the ponderous satellites fill a sector of the housing between about 90 degrees and about 270 degrees.

10. An apparatus according to claim 9, wherein the ponderous satellites fill a sector of the housing of about 180 degrees.

11. An apparatus according to claim 2, wherein the at least one balancing assembly further comprises a dampening means for providing resistance to movement of the plurality of ponderous satellites and for dampening any noise caused by two or more ponderous satellites coming into contact.

12. An apparatus according to claims 11, wherein the dampening means comprises a volume of a liquid that at least partially fills the housing of the at least one balancing assembly.

13. An apparatus according to claim 12, wherein the volume of liquid and the viscosity of the liquid are so selected as to contribute to a substantially accurate balancing and a substantially limited amplitude of a movement of the rotor at a resonance frequency thereof.

14. An apparatus according to claim 12, wherein the volume of liquid fills between about 10% and about 90% of the housing.

15. An apparatus according to claim 12, wherein the viscosity of the liquid is between about 200 cst and about 700 cst.

16. An apparatus according to claim 15, wherein the viscosity of the liquid is about 350 cst.

17. An apparatus according to claim 2, wherein the housing of the at least one balancing assembly comprises a circular cavity having a generally rectangular cross-section.

18. An apparatus according to claim 2, wherein the housing of the at least one balancing assembly comprises a bottom wall, an inner lateral wall, an outer race and a top wall delimiting a circular cavity for containing the plurality of ponderous satellites, and wherein the outer race is made of hardened steel.

19. An apparatus according to claim 4, wherein the plurality of ponderous satellites is made of hardened steel.

20. An apparatus according to claim 1, wherein
the first containing means comprises at least one separation compartment and the second containing means comprises at least one storage container, and
the at least one separation compartment is further apart from the rotation axis than the at least one storage container.

21. An apparatus according to claim 20, wherein the centrifuge comprises a rotor comprising:
a central storage member having a bottom and an upper portion, wherein the at least one storage container is included in the central storage member;
a peripheral storage member surrounding the central storage member and connected to the upper portion thereof, wherein the at least one separation compartment is included in the peripheral storage member; and
a shaft connected to the bottom of the central storage member.

22. An apparatus according to claim 21, wherein the balancing means comprises an upper balancing assembly secured to the rotor around the central storage member underneath the peripheral storage member, so that a plane containing the upper balancing assembly is substantially perpendicular to the rotation axis of the centrifuging means.

23. An apparatus according to claim 21, wherein the balancing means comprises a lower balancing assembly that is connected to the shaft.

24. An apparatus according to claim 1, wherein the liquid transferring means comprises a first transferring means including a pumping means for transferring a separated component from at least one separation bag contained in the first containing means into at least one satellite bag contained in the second containing means.

25. An apparatus according to claim 1, wherein the liquid transferring means comprises a first transferring means including a squeezing means for squeezing at least one separation bag contained in the first containing means so as to cause a transfer of a separated component into at least one satellite bag contained in the second containing means.

26. An apparatus according to claim 25, wherein the squeezing means comprises:
at least one flexible hydraulic chamber included in the first containing means;
a hydraulic pumping station for pumping a hydraulic fluid in and out the at least one hydraulic chamber.

27. An apparatus according to claim 24, further comprising:
a memory for storing a separation speed at which a volume of composite liquid is separated into at least first and second components; and
a control unit programmed for:
receiving the separation speed from the memory;
causing the rotor to rotate at the separation speed and separate a volume of composite liquid in a separation bag contained in the first containing means into at least a first and second components;

causing the first transferring means to transfer at least one portion of the first component into a satellite bag contained in the second containing means, whereby an unbalance of the rotor resulting from the transfer of liquid is substantially neutralized by the balancing means when it occurs.

28. An apparatus according to claim 1, wherein the support means comprises a cradle having:
   a body comprised of a portion of a generally frusto-conical wall inclined with respect to the rotation axis, and
   a bottom wall connected to the frusto-conical wall comprising a curved portion having a concavity oriented towards the rotation axis.

29. An apparatus according to claim 1, wherein the securing means comprises:
   a bag holder having an elongated body having:
      a hanging means for removably holding the least one satellite bag by an upper part thereof; and
      a first locking means for removably securing the elongated body to the inclined wall, and
      a second locking means integral with the inclined wall, complementary to the first locking means.

30. An apparatus according to claim 1, further comprising:
   a memory for storing a transfer speed at which a volume of liquid in a satellite bag contained in the second containing means is transferred into a separation bag contained in the first containing means; and
   a control unit programmed for:
      receiving the transfer centrifugation speed from the memory;
      causing the rotor to rotate at the transfer centrifugation speed so as to transfer at least a portion of a liquid in a satellite bag contained in the second containing means into a separation bag contained in the first containing means, whereby an unbalance of the rotor resulting from the transfer of liquid is substantially neutralized by the balancing means when it occurs.

* * * * *